US009234024B2

(12) United States Patent
Sidhu et al.

(10) Patent No.: US 9,234,024 B2
(45) Date of Patent: Jan. 12, 2016

(54) AFFINITY MATURED CRIG VARIANTS

(75) Inventors: Sachdev S. Sidhu, Toronto (CA); Bing Li, Foster City, CA (US); Menno Van Lookeren Campagne, San Francisco, CA (US); Christian Wiesmann, Brisbane, CA (US)

(73) Assignee: GENENTECH, INC., South San Francisco, CA (US)

( * ) Notice: Subject to any disclaimer, the term of this patent is extended or adjusted under 35 U.S.C. 154(b) by 671 days.

(21) Appl. No.: 12/387,794

(22) Filed: May 6, 2009

(65) Prior Publication Data

US 2010/0150908 A1 Jun. 17, 2010

Related U.S. Application Data

(60) Provisional application No. 61/189,653, filed on Aug. 20, 2008, provisional application No. 61/050,888, filed on May 6, 2008.

(51) Int. Cl.
| C07K 1/00 | (2006.01) |
| C07K 14/00 | (2006.01) |
| C07K 17/00 | (2006.01) |
| C07K 14/705 | (2006.01) |
| A61K 38/00 | (2006.01) |

(52) U.S. Cl.
CPC .......... C07K 14/70503 (2013.01); *A61K 38/00* (2013.01)

(58) Field of Classification Search
None
See application file for complete search history.

(56) References Cited

U.S. PATENT DOCUMENTS

| 4,579,827 A | 4/1986 | Sakamoto et al. |
| 5,650,295 A | 7/1997 | Li et al. |
| 6,022,708 A | 2/2000 | De Sauvage et al. |
| 6,410,708 B1 | 6/2002 | Askenazi et al. |
| 7,192,589 B2 | 3/2007 | Ashkenazi et al. |
| 7,282,565 B2 | 10/2007 | Goddard et al. |

FOREIGN PATENT DOCUMENTS

| EP | 0 199 141 | | 10/1986 |
| EP | 0317050 | | 5/1989 |
| EP | 0 616 812 A1 | | 9/1994 |
| EP | 0 616 812 B1 | | 9/1994 |
| WO | WO 9005537 | | 5/1990 |
| WO | WO 9634943 | | 11/1996 |
| WO | WO 9824897 | | 6/1998 |
| WO | WO 9840483 | | 9/1998 |
| WO | WO 9842739 | | 10/1998 |
| WO | WO 9902561 | | 1/1999 |
| WO | WO 9927098 | | 6/1999 |
| WO | WO 9940100 A1 | | 8/1999 |
| WO | WO 9946281 | | 9/1999 |
| WO | WO 0012703 A2 | | 3/2000 |
| WO | WO 0029583 A2 | | 5/2000 |
| WO | WO 0036102 | | 6/2000 |
| WO | WO 0037638 A2 | | 6/2000 |
| WO | WO 0053758 | | 9/2000 |
| WO | WO 0104311 | | 1/2001 |
| WO | WO 0136432 A2 | | 5/2001 |
| WO | 0140466 | | 6/2001 |
| WO | 02008284 | | 11/2002 |
| WO | WO 02000690 | | 11/2002 |
| WO | WO 2004031105 | | 4/2004 |
| WO | WO 2006042329 | | 4/2006 |
| WO | WO 2008036135 A2 * | | 3/2008 |
| WO | WO 2008137338 | | 11/2008 |

OTHER PUBLICATIONS

Baselga, et al., Anti HER2 humanized monoclonal antibody (MAb) alone and in combination with chemotherapy against human breast carcinoma xenografts, Proceedings of ASCO., vol. 13, Abtract 53, (1994).
Baselga, et al., "Recombinant humanized anti-HER2 antibody (Herceptin) enhances the antitumor activity of paclitaxel and doxorubicin against HER2/neu overexpressing human breast cancer xenografts", Cancer Research 58, pp. 2825-2831, (1998).
Goldhirsch, et al., "Meeting highlights: International consensus panel on the treatment of primary breast cancer", Journal of the national cancer institute, vol. 90, No. 21, pp. 1601-1608, (1998).
Journal of the National Cancer Institute, "Herceptin raises its sights beyond advanced breast cancer", 90(12) 882-883, (1998).
Perez, "Paclitaxel in breast cancer", Mayo Foundation and Mayo Clinic Jacksonville, The Oncologist, vol. 3, pp. 373-389, (1998).
Valero, "Future direction of Neoajuvant therapy for breast cancer", Seminars in Oncology, vol. 25, No. 2, pp. 36-41, (1998).
Molina, et al., Journal of Immunol., 153(2): 789-795, (1994).
Monks, A. et al., "Feasibility of High-Flux Anticancer Drug Screen Using a Diverse Panel of Cultured Human Tumor Cell Lines," Natl. Cancer Inst. 83: 757-766 (1991).
Ozaki et al, "Cutting Edge: Combined Treatment of the TNF-alpha and IFN-gamma causes Redistribution of Junctional Adhesion Molecule in Human Endothelial Cells", J. Immunol., vol.163, No. 2, (1999).
Rudikoff, S et al. Proc Natl Acad Sci USA, 79:1979-1983, (1982).
Schwartz, R., "Costimulation of T Lymphocytes: The Role of CD28, CTLA-4, and B7/BB1 in Interleukin-2 Production and Immunotherapy." Cell. 71(7):1065-1068, (1992).
Skehan, P. et al., "New Colorimetric Cytoxicity Assay. for Anticancer-Drug Screening," J. Natl.Cancer Inst. 82: 1107-1112 (1990).
Skolnick, et al., Trends in biotech., 18: 34-39, (2000).
Spencer, S. et al., "The Orphan Receptor CRF2-4 is an Essential Subunit of the Interleukin 10 Receptor," J. Exp. Med. 187: 571-578 (1998).
Taylor, S. et al., "The Human Homologue of Bub3 Is Required for Kinetochore Localization of Bub1 and a Mad3/Bub1Related Protein Kinase," J. Cell. Biol. 142 (1):1.11 (1998).
Walker MG. 2391g is co-expressed with activated macrophage genes. Biochim Biophys Acta. Apr. 12, 2002;1574(3), 387-390.
Walunas et al., "CTLA-4 Can Function as a Negative Regulator of T Cell Activation." Immunity.1(5):405-413, (1994).

(Continued)

*Primary Examiner* — Daniel E Kolker
*Assistant Examiner* — James Rogers
(74) *Attorney, Agent, or Firm* — Bonny Yeung Hinkle; Ginger R. Dreger; Arnold & Porter LLP

(57) ABSTRACT

The present invention concerns affinity matured CRIg variants. In particular, the invention concerns CRIg variants having increased binding affinity to C3b and retaining selective binding to C3b over C3.

22 Claims, 17 Drawing Sheets

(4 of 17 Drawing Sheet(s) Filed in Color)

(56) References Cited

OTHER PUBLICATIONS

Welt, S. et al., "Phase 1111 Study of Iodine 131-Labeled Monoclonal Antibody A33 in Patients with Advanced Colon Cancer," J. Clin. Oncol. 12: 1561-1571 (1994).
Welt, S. et al., "Quantative Analysis of Antibody Localization in Human Metastatic Colon Cancer: A Phase I Study of Monoclonal Antibody A33," J. Clin. Oncol. 8: 1894-1906 (1990).
Wiesmann, et al., Nature, 444(7116): 217-220, (2006).
Wu, H etal. J. Mol. Biol. [1999] 294:151-162.
Alderson et al., "Molecular and Biological Characterization of Human 4-1BB and Its Ligand." European Journal of Immunology. 24(9):2219-2227 (1994).
Benevenuti et al., Crystallization of Soluble Proteins in Vapor Diffusion for X-ray Crystallography, Nature Protocols, published on-line Jun. 28, 2007, 2(7):1633-1651.
Blast Report, http://expasy.org/cgi-bin/niceprot.pl/printable?ac=Q80WA3, Jun. 1, 2003.
Bowie, et al., Science, 247: 1306-1310 (1990).
Boyum, A. "A One Stage Procedure for Isolation of Granulocytes and Lymphocytes from Human Blood," Norwegian Defense Establishment, Div. of Toxicology, pp. 51-76, 1968.
Casset, F et al. Biochem. Biophys. Res. Comm. [2003] 307:198-205.
Chambers and Allison., "Co-Stimulation in T Cell Responses." Current Opinion in Immunology. 9(3):396-404, (1997).
Cudney, "Protein crystallization and dumb luck", The Rigaku Journal, vol. 16, No. 1, pp. 1-7, (1999).
Database Genebank (Apr. 24, 2001), Ashkenazi et al., "Human Pro 1868 Protein" Database Accession No. AAB80272, XP002448361.
De Smet et al., "The Activation of Human Gene MAGE-1 in Tumor Cells is Correlated with Genome-Wide Demethylation." Proc. Natl. Acad. Sci. USA 93(14):7149-7153, (1996).
Drenth, "Principles of protein x-ray crystallography", $2^{nd}$ Edition, Chapter 1, pp. 1-21, (1999).
Finn and Lotze., "Introduction: Third Keystone Symposium on Cellular Immunology and the Immunotherapy of Cancer." Journal of Immunotherapy. 21(2):114-118 (1998).
Heath, et al., "The human A33 antigen is a transmembrane glycoprotein and a novel member of the immunoglobulin superfamily", PNAS, 94(2): 469-474, (1997).
Hellstrom and Hellstrom., "T Cell Immunity to Tumor Antigens." Critical Reviews in Immunology. 18(1-2):1-6, (1998).
Helmy, et al., Cell, 124(5): 915-927, (2006).
Helmy, et al., Cell, Online: http://www.seiendirect.com, (2006).
Jenkins, M., "The Ups and Downs of T Cell Costimulation." Immunity 1(6):443-446, (1994).
Jun. et al., "The B7 and CD28 Receptor Families." Immunology Today. 15(7):321-331, (1994).
Kahan BD. Immunosuppressive therapy. Curr. Opin Immunol., 4(5):553-560, (1992).
Kim et al. Characterization of monoclonal antibody specific to the Z391g protein, a member of immunoglobulin superfamily. Immunol Lett Jul. 15, 2005;99(2):153-61.
Kundrot, "Which strategy for a protein crystallization project?", Cellular molecular life science, vol. 61, pp. 525-536, (2004).
Kwon et al., "Manipulation of T Cell Costimulatory and Inhibitory Signals for Immunotherapy of Prostate Cancer." Proc. Natl. Acad. Sci. USA 94(15):8099-8103, (1997).
Langnaese, et al., "Cloning of Z391g, a novel gene with immunoglobulin-like domains located on human chromosome XI", BHA, pp. 522-525, (2000).
Linsley and Ledbetter., "The Role of the CD28 Receptor During T Cell Responses to Antigen." Annu. Rev. Immunol 11:191-212, (1993).
Lynch et al., "Flt3 Ligand Induces Tumor Regression and Antitumor Immune Responses in Vivo." Nature Medicine. 3(6):625-631, (1997).
MacCallum, RM et al. J. Mol Biol. 262:732-745, (1996).
Martin-Padura, I. et al, "Junctional Adhesion Molecule, a Novel Member of the lmmunoglobulin Superfamily That Distributes at Intercellular Junctions and Modulates Monocyte Transmigration," J. Cell Biol. 142 (1): 117-27 (1998).
McPherson, Current Approaches to Macromolecular Crystallization. European Journal of Biochemistry, vol. 189, pp. 1-23, (1990).
Melero et al., "Monoclonal Antibodies Against the 4-1BB T-cell Activation Molecule Eradicate Established Tumors." Nature Medicine. 3(6):682-685, (1997).
He, et. al. "A role of macrophage complement receptor CRIg in immune clearance and inflammation", Molecular Immunology, 2008, vol. 45, No. 16, pp. 4041-4047.
Katschke, et. al. "A novel inhibitor of the alernative pathway of complement reverses inflammation and bone destruction in experimental arthritis", J. of Experimental Med., Jun. 11, 2007, vol. 204, No. 6, pp. 1319-1325.
Li, et. al. "Improving Therapeutic Efficacy of a Complement Receptor by Structure-based Affinity Maturation", J. Of Bio. Chem., Dec. 16, 2009, vol. 284, No. 51, pp. 35605-35611.
Ricklin, et. al. "Complement-targeted therapeutics.", Nature Biotechnology, 2007, vol. 25, No. 11, pp. 1265-1275.
Vogt, et. al. "VSIG4, a B7 family-related protein, is a negative regulator of T cell activation", J. of Clin. Invest., Oct. 2006, vol. 116, No. 10, pp. 2817-2826.

\* cited by examiner

```
1101  TAGTTTCTC CCTGGCTTCC TTTCTTCTTA GACAACCTAA AGTATCACTAC TAGTCTGCCA ATTCTGCCGC CATTGAGAAA TCTCTGGTTT GCCTAAGAAT
      ATCGAAGAG GGACCGAAGG AAAGAAGAAT CTGTTGGATT TCATAGATAG ATCAGACGGT TAAGACCCCG GTAACTCTTT AGGACCAAA CCGATTCTTA

1201  ATACTACATG CACCTGAAGA AATCTAGCTT CTCGGCTTCA CCCAGAACAA TTTTCTTGCT AGGGCCTTCA CAACTCTCT CCAAACAGGA GAGAAATTCC
      TATGATGTAC GTGGAGTTCT TTAGATCGAA GAGCCCGAAGT GGGTCTTGTT AAAAGAAGGA TCCCGGAAGT GTTGAGAAGA GGTTTGTCGT CTCTTTAAGG

1301  ATAGGAGTAG AGGTTCTTTA TCATGCCTCC AGACAGGGTG AGTCTCAGTC CTACAAACTC AGACAACACAC ATGGGTCTAG TACCCAGATC CTTTCTCTAG
      TATCGTCATC TCCAAGAAAT AGTACGGAGG TCTGTCCCAC TCAGAGTCAG GATGTTTGAG TCTGTTGTG CTAATGAGAA GAAAGAGATC

1401  GGCCAGATGA CTTTTAATTG ATATTACTAT TGCTACATTA TCAATCTAAT GCAGATGTAT TCTTTTGTTG TTAATAAATG TTAATCATG ACATCAAAAA
      CCGGTCTACT GAAAATTAAC TATAATGATA ACGATGTAAT ACTTAGATTA CGTATACATA AGAAACAAC AATTATTAC AAATTAGTAC TGTAGTTTTT

1501  AAAAAAAAA AAGGCGCGCC CCGACTCTAG AGTCGAGCCTG CAGTAGGGAT AACAGGGTAA TAAGCTTGCC CCCATGGCC CAACTTGTTT
      TTTTTTTTT TTCCGCGCGG GGCTGAGATC TCAGCTGGAC GTCATCCCTA TTGTCCCATT ATTCGAACCG GGGGTACCGG GTTGAACAAA
      *pRK5 continues here
```

FIG. 3C

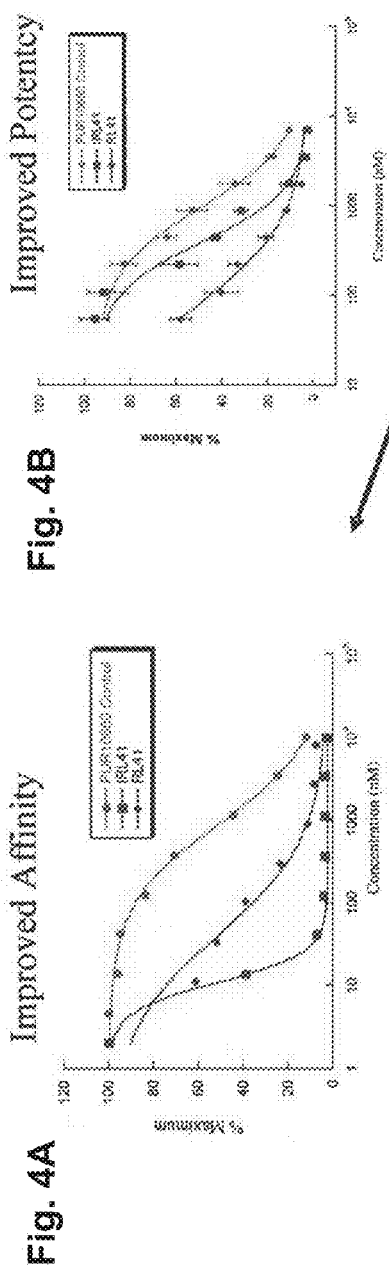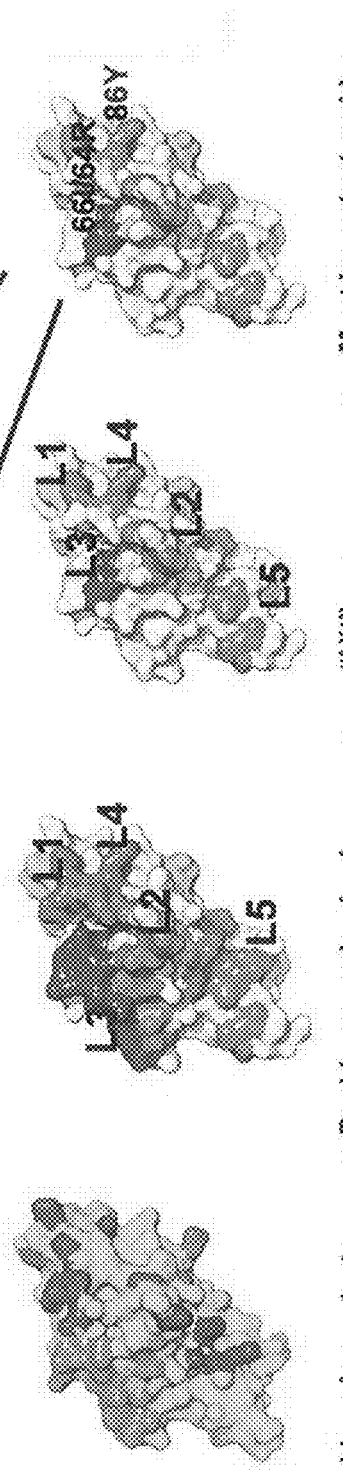
Structure-based affinity maturation of CRIg to generate a more potent inhibitor
Fig. 4A — Impro The correlated between competitive ELISA and Hemolytic Assay

Improved affinity of the Q64R / M86Y CRIg mutant

Improved complement inhibitory potency of CRIg Q64R / M86Y *in vitro* compared to wildtype CRIg

CRIg Q64R/M86Y shows improved efficacy *in vivo* over CRIg WT *in vivo*

Table 1. Phage Libraries

| Library | Position | Diversity |
|---|---|---|
| Library 1 | E8-K15 | $1.2 \times 10^{10}$ |
| Library 2 | R41-T47 | $1.4 \times 10^{10}$ |
| Library 3 | S54-Q64 | $1.6 \times 10^{10}$ |
| Library 4 | E85-Q99 | $1.2 \times 10^{10}$ |
| Library 5 | Q105-K111 | $1.9 \times 10^{10}$ |

Fig. 10

| | Name | Mutations | Competitive ELISA | | Hemolysis Inhibition | |
|---|---|---|---|---|---|---|
| | | | Mut. IC50 mAb w/ epitope (nM) | WT/Mu. | Mut. IC50 W/ Poly(nM) | W/T(IC50) |
| Library 1 | L11 | E5Y | 384 | 0.9X | 439 | 1X |
| | L12 | E5W | 142 | 2X | 176 | 4X |
| | L13 | W14F | 882 | 0.4X | 293 | 2X |
| | L15 | E5Y/W14F | 1274 | 0.3X | 310 | 2X |
| Library 2 | L21 | G42D | 453 | 0.7X | 378 | 1X |
| | L22 | D44H | 338 | 1X | 1207 | 0.5X |
| | L23 | P45F | 1266 | 0.3X | 358 | 1.5X |
| | L24 | G42D/D44H/P45F | 238 | 1X | 227 | 2X |
| Library 3 | L31 | Q60I | 388 | 0.9X | 78 | 5X |
| | L32 | Q64R | 34 | 10X | 293 | 2X |
| | L33 | Q60I/Q64R | 255 | 1X | 51 | 10X |
| Library 4 | L

Fig. 13

AFFINITY MATURED CRIG VARIANTS

The present application claims the benefit of U.S. Provisional Patent Application Ser. No. 61/189,653, filed Aug. 20, 2008 and U.S. Provisional Patent Application Ser. No. 61/050,888, filed May 6, 2008, the disclosures of which are incorporated hereby by reference in their entirety. We hereby expressly incorporate herein by reference, in its entirety, the last-filed (filed May 6, 2009) computer readable Sequence Listing, saved as "GNE-0322US.TXT", date of creation May 4, 2009, size 44 KB, submitted in U.S. application Ser. No. 12/387,794.

INCORPORATION OF SEQUENCE LISTING

This application includes a Sequence Listing submitted via EFS-Web as a computer-readable form 44,900 byte file entitled "GNE322USseqlist.txt" created on Feb. 15, 2012, which is hereby incorporated herein by reference in its entirety.

FIELD OF THE INVENTION

The present invention concerns affinity matured CRIg variants. In particular, the invention concerns CRIg variants having increased binding affinity to C3b and retaining selective binding to C3b over C3.

BACKGROUND OF THE INVENTION

The Complement System

The complement system is a complex enzyme cascade made up of a series of serum glycoproteins that normally exist in inactive, pro-enzyme form. Three main pathways, the classical, alternative and mannose-binding lectin pathway, can activate complement, which merge at the level of where two similar C3 convertases cleave C3 into C3a and C3b.

Macrophages are specialist cells that have developed an innate capacity to recognize subtle differences in the structure of cell-surface expressed identification tags, so called molecular patterns (Taylor, et al., *Eur J Immunol* 33, 2090-1097 (2003); Taylor, et al., *Annu Rev Immunol* 23, 901-944 (2005)). While the direct recognition of these surface structures is a fundamental aspect of innate immunity, opsonization allows generic macrophage receptors to mediate engulfment, increasing the efficiency and diversifying recognition repertoire of the phagocyte (Stuart and Ezekowitz, *Immunity* 22, 539-550 (2005)). The process of phagocytosis involves multiple ligand-receptor interactions, and it is now clear that various opsonins, including immunoglobulins, collectins, and complement components, guide the cellular activities required for pathogen internalization through interaction with macrophage cell surface receptors (reviewed by Aderem and Underhill, *Annu Rev Immunol* 17, 593-623 (1999); Underhill and Ozinsky, *Annu Rev Immunol* 20, 825-852 (2002)). While natural immunoglobulins encoded by germline genes can recognize a wide variety of pathogens, the majority of opsonizing IgG is generated through adaptive immunity, and therefore efficient clearance through Fc receptors is not immediate (Carroll, *Nat Immunol* 5, 981-986 (2004)). Complement, on the other hand, rapidly recognizes pathogen surface molecules and primes the particle for uptake by complement receptors (Brown, *Infect Agents Dis* 1, 63-70 (1991)).

Complement consists of over 30 serum proteins that opsonize a wide variety of pathogens for recognition by complement receptors. Depending on the initial trigger of the cascade, three pathways can be distinguished (reviewed by (Walport, *N Engl J Med* 344, 1058-1066 (2001)). All three share the common step of activating the central component C3, but they differ according to the nature of recognition and the initial biochemical steps leading to C3 activation. The classical pathway is activated by antibodies bound to the pathogen surface, which in turn bind the C1q complement component, setting off a serine protease cascade that ultimately cleaves C3 to its active form, C3b. The lectin pathway is activated after recognition of carbohydrate motifs by lectin proteins. To date, three members of this pathway have been identified: the mannose-binding lectins (MBL), the SIGN-R1 family of lectins and the ficolins (Pyz et al., *Ann Med* 38, 242-251 (2006)) Both MBL and ficolins are associated with serine proteases, which act like C1 in the classical pathway, activating components C2 and C4 leading to the central C3 step. The alternative pathway contrasts with both the classical and lectin pathways in that it is activated due to direct reaction of the internal C3 ester with recognition motifs on the pathogen surface. Initial C3 binding to an activating surface leads to rapid amplification of C3b deposition through the action of the alternative pathway proteases Factor B and Factor D. Importantly, C3b deposited by either the classical or the lectin pathway also can lead to amplification of C3b deposition through the actions of Factors B and D. In all three pathways of complement activation, the pivotal step in opsonization is conversion of the component C3 to C3b. Cleavage of C3 by enzymes of the complement cascades exposes the thioester to nucleophilic attack, allowing covalent attachment of C3b onto antigen surfaces via the thioester domain. This is the initial step in complement opsonization. Subsequent proteolysis of the bound C3b produces iC3b, C3c and C3dg, fragments that are recognized by different receptors (Ross and Medof, *Adv Immunol* 37, 217-267 (1985)). This cleavage abolishes the ability of C3b to further amplify C3b deposition and activate the late components of the complement cascade, including the membrane attack complex, capable of direct membrane damage. However, macrophage phagocytic receptors recognize C3b and its fragments preferentially; due to the versatility of the ester-bond formation, C3-mediated opsonization is central to pathogen recognition (Holers et al., *Immunol Today* 13, 231-236 (1992)), and receptors for the various C3 degradation products therefore play an important role in the host immune response.

C3 itself is a complex and flexible protein consisting of 13 distinct domains. The core of the molecule is made up of 8 so-called macroglobulin (MG) domains, which constitute the tightly packed α and β chains of C3. Inserted into this structure are CUB (C1r/C1s, Uegf and Bone mophogenetic protein-1) and TED domains, the latter containing the thioester bond that allows covalent association of C3b with pathogen surfaces. The remaining domains contain C3a or act as linkers and spacers of the core domains. Comparison of C3b and C3c structures to C3 demonstrate that the molecule undergoes major conformational rearrangements with each proteolysis, which exposes not only the TED, but additional new surfaces of the molecule that can interact with cellular receptors (Janssen and Gros, *Mol Immunol* 44, 3-10 (2007)).

Complement C3 Receptors on Phagocytic Cells

There are three known gene superfamilies of complement receptors: The short consensus repeat (SCR) modules that code for CR1 and CR2, the beta-2 integrin family members CR3 and CR4, and the immunoglobulin Ig-superfamily member CRIg.

CR1 is a 180-210 kDa glycoprotein consisting of 30 Short Consensus Repeats (SCRs) and plays a major role in immune complex clearance. SCRs are modular structures of about 60 amino acids, each with two pairs of disulfide bonds providing structural rigidity. High affinity binding to both C3b and C4b occurs through two distinct sites, each composed of 3 SCRs reviewed by (Krych-Goldberg and Atkinson, *Immunol Rev* 180, 112-122 (2001)). The structure of the C3b binding site, contained within SCR 15-17 of CR1 (site 2), has been determined by MRI (Smith et al., *Cell* 108, 769-780 (2002)), revealing that the three modules are in an extended head-to-tail arrangement with flexibility at the 16-17 junction. Structure-guided mutagenesis identified a positively charged surface region on module 15 that is critical for C4b binding. This patch, together with basic side chains of module 16 exposed on the same face of CR1, is required for C3b binding. The main function of CR1, first described as an immune adherence receptor (Rothman et al., *J Immunol* 115, 1312-1315 (1975)), is to capture ICs on erythrocytes for transport and clearance by the liver (Taylor et al., *Clin Immunol Immunopathol* 82, 49-59 (1997)). There is a role in phagocytosis for CR1 on neutrophils, but not in tissue macrophages (Sengelov et al., *J Immunol* 153, 804-810 (1994)). In addition to its role in clearance of immune complexes, CR1 is a potent inhibitor of both classical and alternative pathway activation through its interaction with the respective convertases (Krych-Goldberg and Atkinson, 2001, supra; Krych-Goldberg et al., *J Biol Chem* 274, 31160-31168 (1999)). In the mouse, CR1 and CR2 are two products of the same gene formed by alternative splicing and are primarily associated with B-lymphocytes and follicular dendritic cells and function mainly in regulating B-cell responses (Molina et al., 1996). The mouse functional equivalent of CR1, Crry, inactivates the classical and alternative pathway enzymes and acts as an intrinsic regulator of complement activation rather than as a phagocytic receptor (Molina et al., *Proc Natl Acad Sci USA* 93, 3357-3361 (1992)).

CR2 (CD21) binds iC3b and C3dg and is the principal complement receptor that enhances B cell immunity (Carroll, *Nat Immunol* 5, 981-986 (2004); Weis et al., *Proc Natl Acad Sci USA* 81, 881-885 (1984)). Uptake of C3d-coated antigen by cognate B cells results in an enhanced signal via the B cell antigen receptor. Thus, coengagement of the CD21-CD19-CD81 coreceptor with B cell antigen receptor lowers the threshold of B cell activation and provides an important survival signal (Matsumoto et al., *J Exp Med* 173, 55-64 (1991)). The CR2 binding site on iC3b has been mapped partly on the interface between the TED and the MG1 domains (Clemenza and Isenman, *J Immunol* 165, 3839-3848 (2000)).

CR3 and CR4 are transmembrane heterodimers composed of an alpha subunit (CD11b or $\alpha_M$ and CD11c or $\alpha_x$, respectively) and a common beta chain (CD18 or $\beta_2$), and are involved in adhesion to extracellular matrix and to other cells as well as in recognition of iC3b. They belong to the integrin family and perform functions not only in phagocytosis, but also in leukocyte trafficking and migration, synapse formation and costimulation (reviewed by (Ross, *Adv Immunol* 37, 217-267 (2000)). Integrin adhesiveness is regulated through a process called inside-out signaling, transforming the integrins from a low- to a high-affinity binding state (Liddington and Ginsberg, *J Cell Biol* 158, 833-839 (2002)). In addition, ligand binding transduces signals from the extracellular domain to the cytoplasm. The binding sites of iC3b have been mapped to several domains on the alpha chain of CR3 and CR4 (Diamond et al., *J Cell Biol* 120, 1031-1043 (1993); Li and Zhang, *J Biol Chem* 278, 34395-34402 (2003); Xiong and Zhang, *J Biol Chem* 278, 34395-34402 (2001)). The multiple ligands for CR3: iC3b, beta-glucan and ICAM-1, seem to bind to partially overlapping sites contained within the I domain of CD11b (Balsam et al., 1998; Diamond et al., 1990; Zhang and Plow, 1996). Its specific recognition of the proteolytically inactivated form of C3b, iC3b, is predicted based on structural studies that locate the CR3 binding sites to residues that become exposed upon unfolding of the CUB domain in C3b (Nishida et al., *Proc Natl Acad Sci USA* 103, 19737-19742 (2006)), which occurs upon $\alpha'$ chain cleavage by the complement regulatory protease, Factor I.

CRIg is a macrophage associated receptor with homology to A33 antigen and JAM1 that is required for the clearance of pathogens from the blood stream. A human CRIg protein was first cloned from a human fetal cDNA library using degenerate primers recognizing conserved Ig domains of human JAM1. Sequencing of several clones revealed an open reading frame of 400 amino acids. Blast searches confirmed similarity to Z39Ig, a type 1 transmembrane protein (Langnaese et al., *Biochim Biophys Acta* 1492 (2000) 522-525). The extracellular region of this molecule was found to consist of two Ig-like domains, comprising an N-terminal V-set domain and a C-terminal C2-set domain. The novel human protein was originally designated as a "single transmembrane Ig superfamily member macrophage associated" (huSTIgMA). (huSTIgMA). Subsequently, using 3' and 5' primers, a splice variant of huSTIgMA was cloned, which lacks the membrane proximal IgC domain and is 50 amino acids shorter. Accordingly, the shorter splice variant of this human protein was designated huSTIgMAshort. The amino acid sequence of huSTIgMA (referred to as PRO362) and the encoding polynucleotide sequence are disclosed in U.S. Pat. No. 6,410,708, issued Jun. 25, 2002. In addition, both huSTIgMA and huSTIgMAshort, along with the murine STIgMA (muSTIgMA) protein and nucleic acid sequences, are disclosed in PCT Publication WO 2004031105, published Apr. 15, 2004.

The crystal structure of CRIg and a C3b:CRIg complex is disclosed in U.S. Application Publication No. 2008/0045697, published Feb. 21, 2008.

The Kupffer cells (KCs), residing within the lumen of the liver sinusoids, form the largest population of macrophages in the body. Although KCs have markers in common with other tissue resident macrophages, they perform specialized functions geared towards efficient clearance of gut-derived bacteria, microbial debris, bacterial endotoxins, immune complexes and dead cells present in portal vein blood draining from the microvascular system of the digestive tract (Bilzer et al., *Liver Int* 26, 1175-1186 (2006)). Efficient binding of pathogens to the KC surface is a crucial step in the first-line immune defense against pathogens (Benacerraf et al., *J Exp Med* 110, 27-48 (1959)). A central role for KCs in the rapid clearance of pathogens from the circulation is illustrated by the significantly increased mortality in mice depleted of KCs (Hirakata et al., *Infect Immun* 59, 289-294 (1991)). The identification of CRIg further stresses the critical role of complement and KCs in the first line immune defense against circulating pathogens.

The only complement C3 receptors identified on mouse KCs are CRIg and CR3 (Helmy et al., *Cell* 124, 915-927 (2006)), while human KCs show additional expression of CR1 and CR4 (Hinglais et al., 1989). Both CRIg and CR3 on KCs contribute to binding to iC3b opsonized particles in vitro (Helmy et al., *Lab Invest* 61, 509-514 (2006)). In vivo, a role of KC-expressed CR3 in the binding to iC3b-coated pathogens is less clear. CR3 has been proposed to contribute to clearance of pathogens indirectly via recruitment of neutrophils and interaction with neutrophil-expressed ICAMI (Conlan and North, *Exp Med* 179, 259-268 (1994); Ebe et al., *Pathol Int* 49, 519-532 (1999); Gregory et al., *J Immunol* 157, 2514-2520 (1996); Gregory and Wing, *J Leukoc Biol* 72, 239-248 (2002); Rogers and Unanue, *Infect Immun* 61, 5090-

5096 (1993)). In contrast, CRIg performs a direct role by capturing pathogens that transit through the liver sinusoidal lumen (Helmy et al., 2006, supra). A difference in the biology of CRIg vs CR3 is in part reflected by difference in binding characteristics of these two receptors. CRIg expressed on KCs constitutively binds to monomeric C3 fragments whereas CR3 only binds to iC3b-opsonized particles (Helmy et al., 2006, supra). The capacity of CRIg to efficiently capture monomeric C3b and iC3b as well as C3b/iC3b-coated particles reflects the increased avidity created by a multivalent interaction between CRIg molecules concentrated at the tip of membrane extensions of macrophages (Helmy et al., 2006, supra) and multimers of C3b and iC3b present on the pathogen surface. While CR3 only binds iC3b-coated particles, CRIg additionally bind to C3b, the first C3 cleavage product formed on serum-opsonized pathogens (Croize et al., *Infect Immun* 61, 5134-5139 (1993)). Since a large number of C3b molecules bound to the pathogen surface are protected from cleavage by factor H and I (Gordon et al., *J Infect Dis* 157, 697-704 (1988)), recognition of C3b ligands by CRIg ensures rapid binding and clearance. Thus, while both CRIg and CR3 are expressed on KCs, they show different ligand specificity, distinct binding properties and distinct kinetics of pathogen clearance.

Examples of pathogens that exploit cell surface receptors for cellular entry are viruses like human immunodeficiency virus (HIV), and intracellular bacteria like *Mycobacterium tuberculosum, Mycobacterium leprae, Yersinia pseudotuberculosis, Salmonella typhimurium* and *Listeria Monocytogenes* and parasites like the prostigmatoid Leishmania major (Cossart and Sansonetti, *Science* 304:242-248 (2004); Galan, *Cell* 103:363-366 (2000); Hornef et al., *Nat. Immunol.* 3:1033-1040 (2002); Stoiber et al., *Mol. Immunol.* 42:153-160 (2005)).

As discussed above, CRIg is a recently discovered complement C3 receptor expressed on a subpopulation of tissue resident macrophages. Next to functioning as a complement receptor for C3 proteins, the extracellular IgV domain of CRIg selectively inhibits the alternative pathway of complement by binding to C3b and inhibiting proteolytic activation of C3 and C5. However, CRIg binding affinity for the convertase subunit C3b is low (IC50>1 μM) requiring a relatively high concentration of protein to reach near complete complement inhibition. Accordingly, there is a need for CRIg polypeptides with improved therapeutic efficacy. The present invention provides such polypeptides.

SUMMARY OF THE INVENTION

The present invention is based, at least in part, on the construction of a CRIg variant with enhanced binding affinity. A CRIg-ECD protein with combined amino acid substitutions Q64R and M86Y showed a 30 fold increased binding affinity and a 7 fold improved complement inhibitory activity over the wildtype CRIg variant. In addition, treatment with the affinity-improved CRIg fusion protein in a mouse model of arthritis resulted in a significant reduction in clinical scores compared to treatment with a wild-type CRIg protein Accordingly, the present invention concerns CRIg variants.

In one aspect, the invention concerns a CRIg variant comprising an amino acid substitution in a region selected from the group consisting of E8-K15, R41-T47, S54-Q64, E85-Q99, and Q105-K111 of the amino acid sequence of SEQ ID NO: 68.

In one embodiment, the variant selectively binds to C3b over C3, or a fragment thereof.

In another embodiment, the variant has increased binding affinity to C3b over native sequence human CRIg of SEQ ID NO: 2, where the binding affinity may, for example, be increased by at least 2 fold, or by at least 3 fold, or by at least 4 fold, or by at least 5 fold, or by at least 6 fold, or by at least 7 fold, or by at least 9 fold, or by at least 10 fold, or by at least 15 fold, or by at least 20 fold, or by at least 30 fold, or by at least 40 fold, or by at least 50 fold, or by at least 70 fold, or by at least 80 fold, or by at least 90 fold, or by at least 100 fold.

In yet another embodiment, the variant is a more potent inhibitor of the alternative complement pathway than native sequence human CRIg of SEQ ID NO: 2.

In a further embodiment, the variant comprises an amino acid substitution at one or more amino acid positions selected from the group consisting of positions 8, 14, 18, 42, 44, 45, 60, 64, 86, 99, 105, and 110 in the amino acid sequence of SEQ ID NO: 68.

In a still further embodiment, the variant comprises an amino acid substitution at one or more of amino acid positions 60, 64, 86, 99, 105 and 110 in the amino acid sequence of SEQ ID NO: 68.

In an additional embodiment, the variant comprises one or more substitutions selected from the group consisting of E8W, W14F, E84Y/W14F; P45F; G42D/D44H/P45F; Q60I; Q64R; Q60I/Q64R; M86Y; M86W, M86F, M86W/Q9R; M86F/Q99R; K110D, K11N; Q105R/K110N; Q105R/K110Q; and Q105K/K110D.

In another embodiment, the variant comprises one or more substitutions selected from the group consisting of Q64R/M86Y; Q60I/Q64R/E8Y; Q60I/Q64R/G42D; Q60I/Q64R/P45F; Q60I/Q64R/G42D/D44H/P45F; Q60I/Q64R/M86Y; Q60I/Q64R/Q105R; Q60I/Q64R/Q105K; Q60I/Q64R/K110N; Q60I/Q105R/K110N; M86Y/E8Y; M86Y/G42D/D44H/P45F; M86Y/P45F; M86Y/G42D/D44H/P45F; M86Y/Q99K; M86Y/Q99; M86Y/Q105R; M86Y/Q105K; and M86Y/Q105R/K110N.

In yet another embodiment, the variant comprises one or more substitutions selected from the group consisting of Q60I; Q64R; Q60I/Q64R; M86Y; Q99L; Q105K/K110D; E8W/Q105R/K110N; Q64R/M86Y; Q60I/Q64R/E8Y; Q60I/Q64R/G42D; Q60I/Q64R/P45F; Q60I/Q64R/G42D/D44H/P45F; Q60I/Q64R/M86Y; Q60I/Q64R/Q105R; Q60I/Q64R/Q105K; Q60I/Q64R/K110N; M86Y/P45F; and M86Y/Q105K.

In a more specific embodiment, the variant comprises a Q60I/Q64R/M86Y or Q60I/Q64R/G42D/D44H/P45F substitution.

In another aspect, the invention concerns a chimeric comprising a CRIg variant as defined herein.

In one embodiment, the chimeric molecule is an immunoadhesin.

In another embodiment, the immunoadhesin comprises a CRIg variant that is shorter than the full-length CRIg of SEQ ID NO: 2.

In yet another embodiment, the chimeric molecule comprises a CRIg extracellular domain.

In a further aspect, the invention concerns a pharmaceutical composition comprising a CRIg variant or a chimeric molecule, e.g. an immunoadhesin of the present invention, in admixture with a pharmaceutically acceptable excipient.

In a still further aspect, the invention concerns a method for the prevention or treatment of a complement-associated disease or condition, comprising administering to a subject in need of such treatment a prophylactically or therapeutically effective amount of a CRIg variant or a chimeric molecule, such as an immunoadhesin, comprising such variant.

In one embodiment, the complement-associated disease is an inflammatory disease or an autoimmune disease.

In another embodiment, the complement-associated disease is selected from the group consisting of rheumatoid arthritis (RA), adult respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulemia, antiphospholipid syndrome, age-related macular degeneration, uveitis, diabetic retinopathy, allo-transplantation, hyperacute rejection, hemodialysis, chronic occlusive pulmonary distress syndrome (COPD), asthma, aspiration pneumonia, utricaria, chronic idiopathic utricaria, hemolytic uremic syndrome, endometriosis, cardiogenic shock, ischemia reperfusion injury, and multiple schlerosis (MS).

In yet another embodiment, the complement-associated disease is selected from the group consisting of inflammatory bowel disease (IBD), systemic lupus erythematosus, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vaculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic polyneuropathy, hepatobiliary diseases such as infectious hepatitis (hepatitis A, B, C, D, E and other nonhepatotropic viruses), autoimmune chronic active hepatitis, primary biliary cirrhosis, granulomatous hepatitis, and sclerosing cholangitis, inflammatory and fibrotic lung diseases (e.g., cystic fibrosis), gluten-sensitive enteropathy, Whipple's disease, autoimmune or immune-mediated skin diseases including bullous skin diseases, erythema multiforme and contact dermatitis, psoriasis, allergic diseases of the lung such as eosinophilic pneumonia, idiopathic pulmonary fibrosis and hypersensitivity pneumonitis, transplantation associated diseases including graft rejection, graft-versus host disease, Alzheimer's disease, paroxysmal nocturnal hemoglobinurea, hereditary angioedema, atherosclerosis and type II membranoproliferative glomerulonephritis.

In a preferred embodiment, the complement-associated disease is rheumatoid arthritis (RA).

In another preferred embodiment, the complement-associated disease is a complement-associated eye condition.

In a further embodiment, the complement-associated eye condition is selected from the group consisting of all stages of age-related macular degeneration (AMD), uveitis, diabetic and other ischemia-related retinopathies, endophthalmitis, and other intraocular neovascular diseases.

In a still further embodiment, the intraocular neovascular disease is selected from the group consisting of diabetic macular edema, pathological myopia, von Hippel-Lindau disease, histoplasmosis of the eye, Central Retinal Vein Occlusion (CRVO), corneal neovascularization, and retinal neovascularization.

In yet another embodiment, the complement-associated eye condition is selected from the group consisting of age-related macular degeneration (AMD), choroidal neovascularization (CNV), diabetic retinopathy (DR), and endophthalmitis, where AMD includes both wet and dry or atrophic AMD.

In one embodiment, the patient is a mammal, preferable a human.

In another aspect, the invention concerns a method for inhibition of the production of C3b complement fragment in a mammal comprising administering to said mammal an effective amount of a CRIg variant of the present invention, or an immunoadhesin comprising such variant.

In yet another aspect, the invention concerns a method for selective inhibition of the alternative complement pathway in a mammal, comprising administering to said mammal an effective amount of a CRIg variant of the present invention, or an immunoadhesin comprising such variant.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1A:
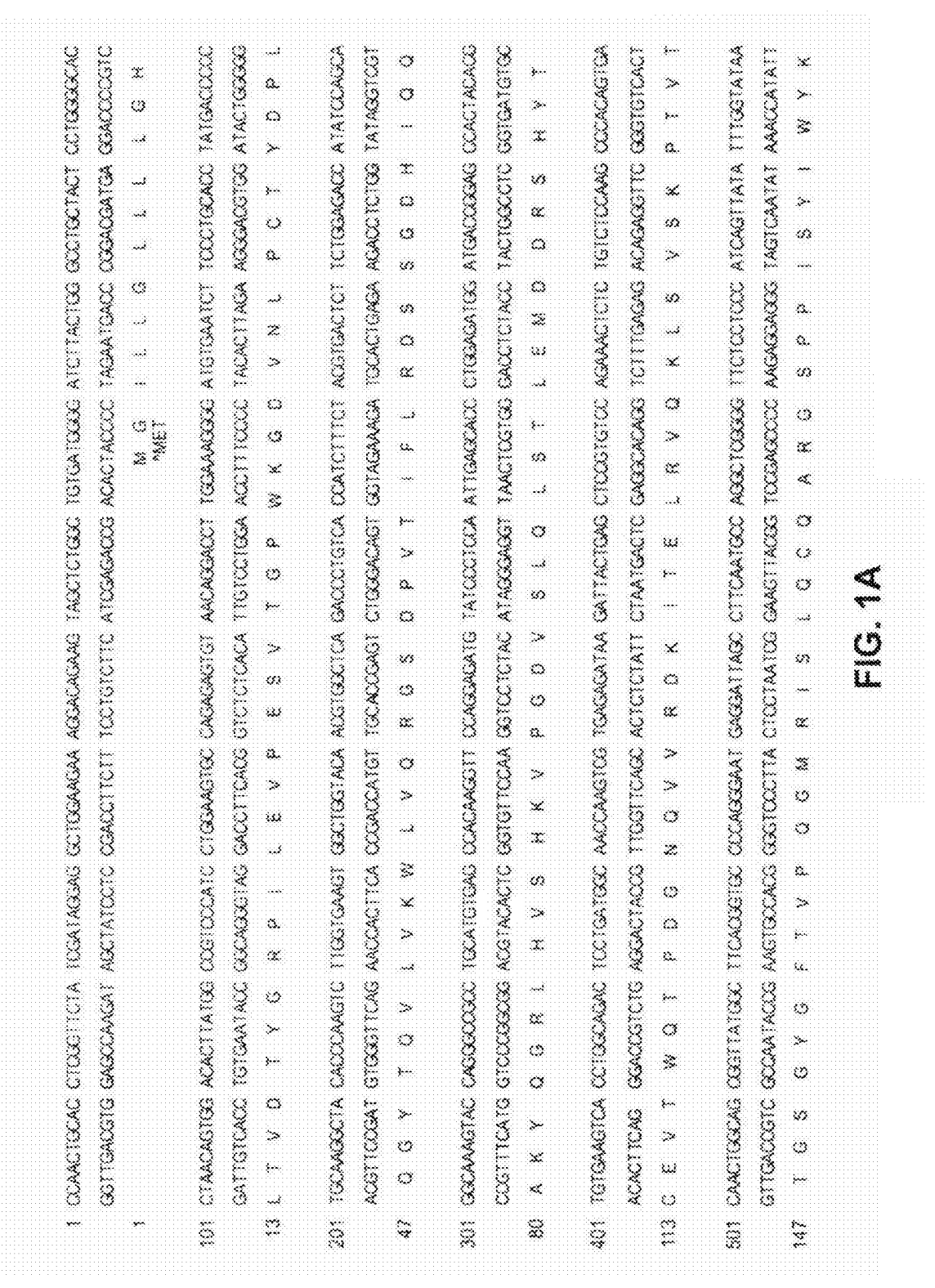
Figure 1B:
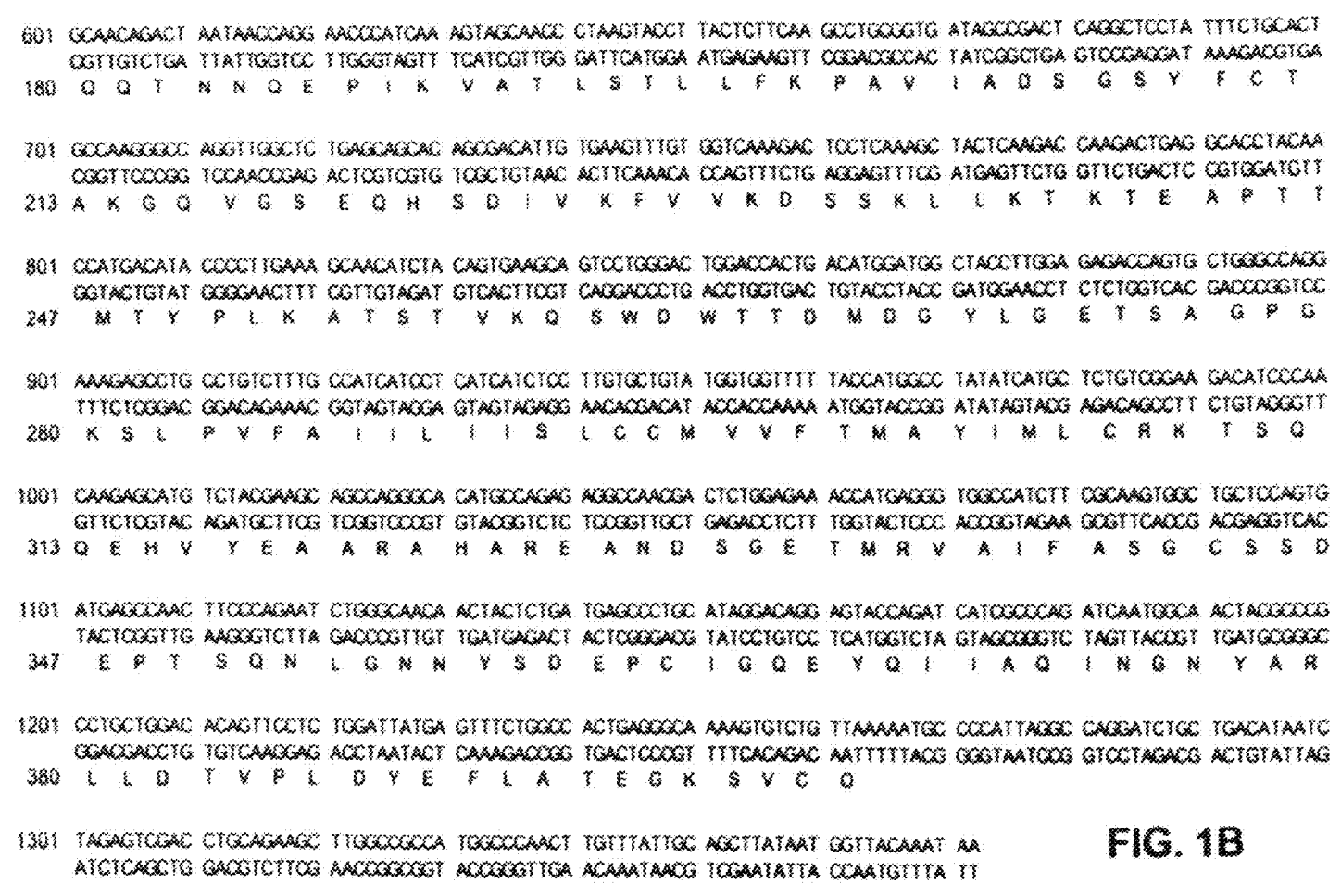

FIG. 1A-1B show the nucleotide and amino acid sequences of the 399-amino acid full-length long form of native human CRIg (huCRIg, SEQ ID NOS: 1 and 2, respectively).

Figure 2A:
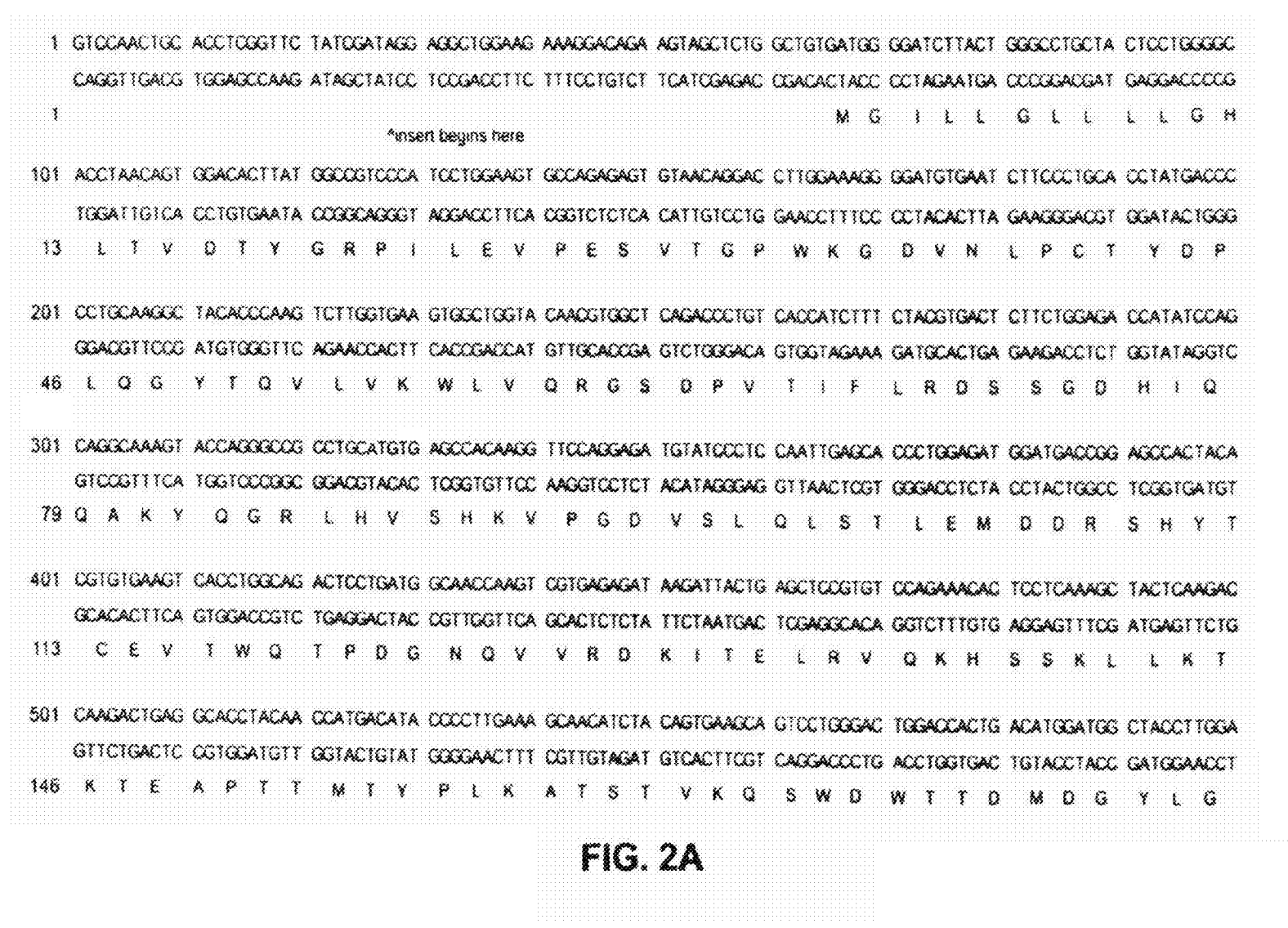
Figure 2B:
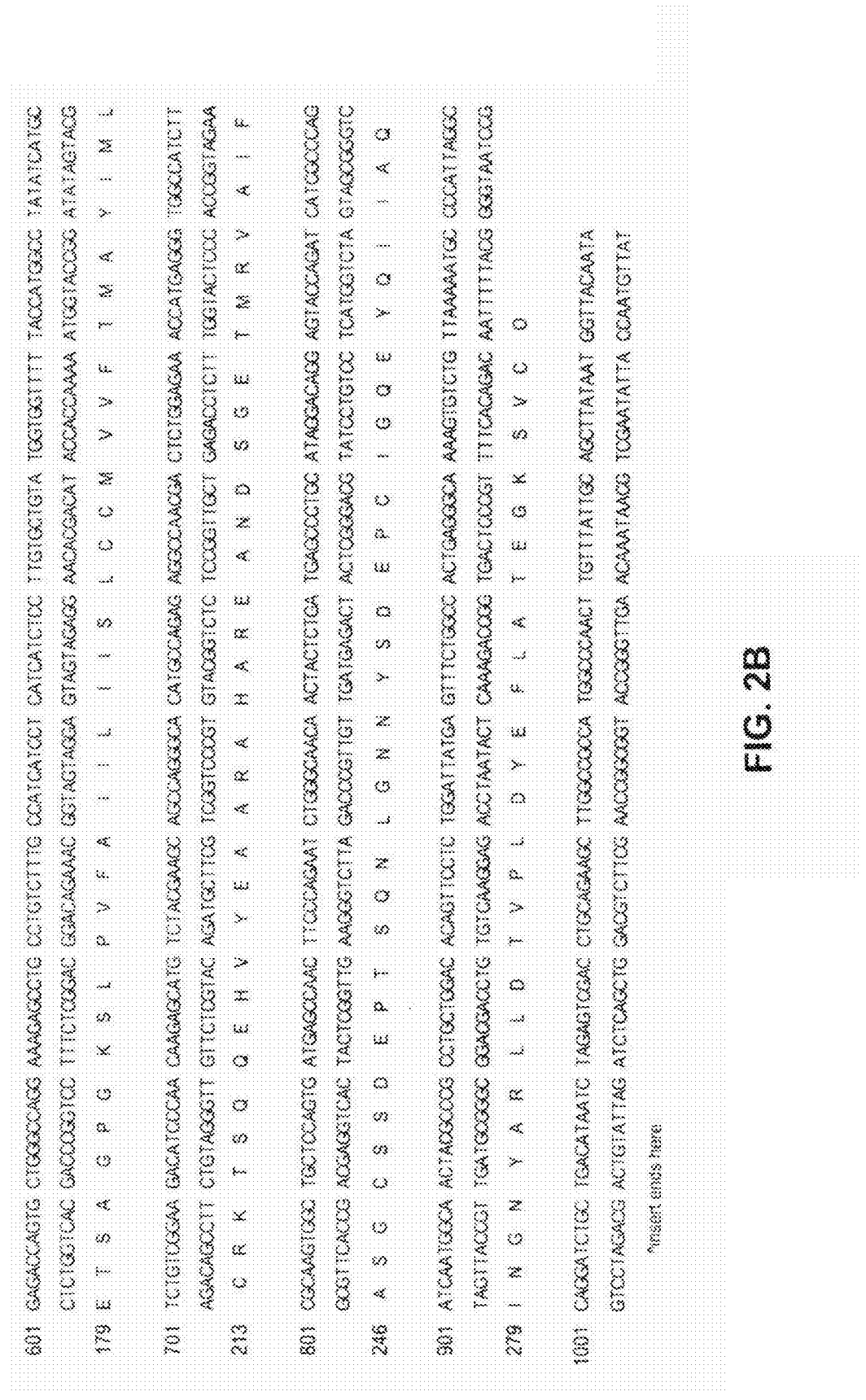

FIG. 2A-2B show the nucleotide and amino acid sequences of the 305-amino acid short form of native human CRIg (huCRIg-short, SEQ ID NOS: 3 and 4, respectively).

Figure 3A:
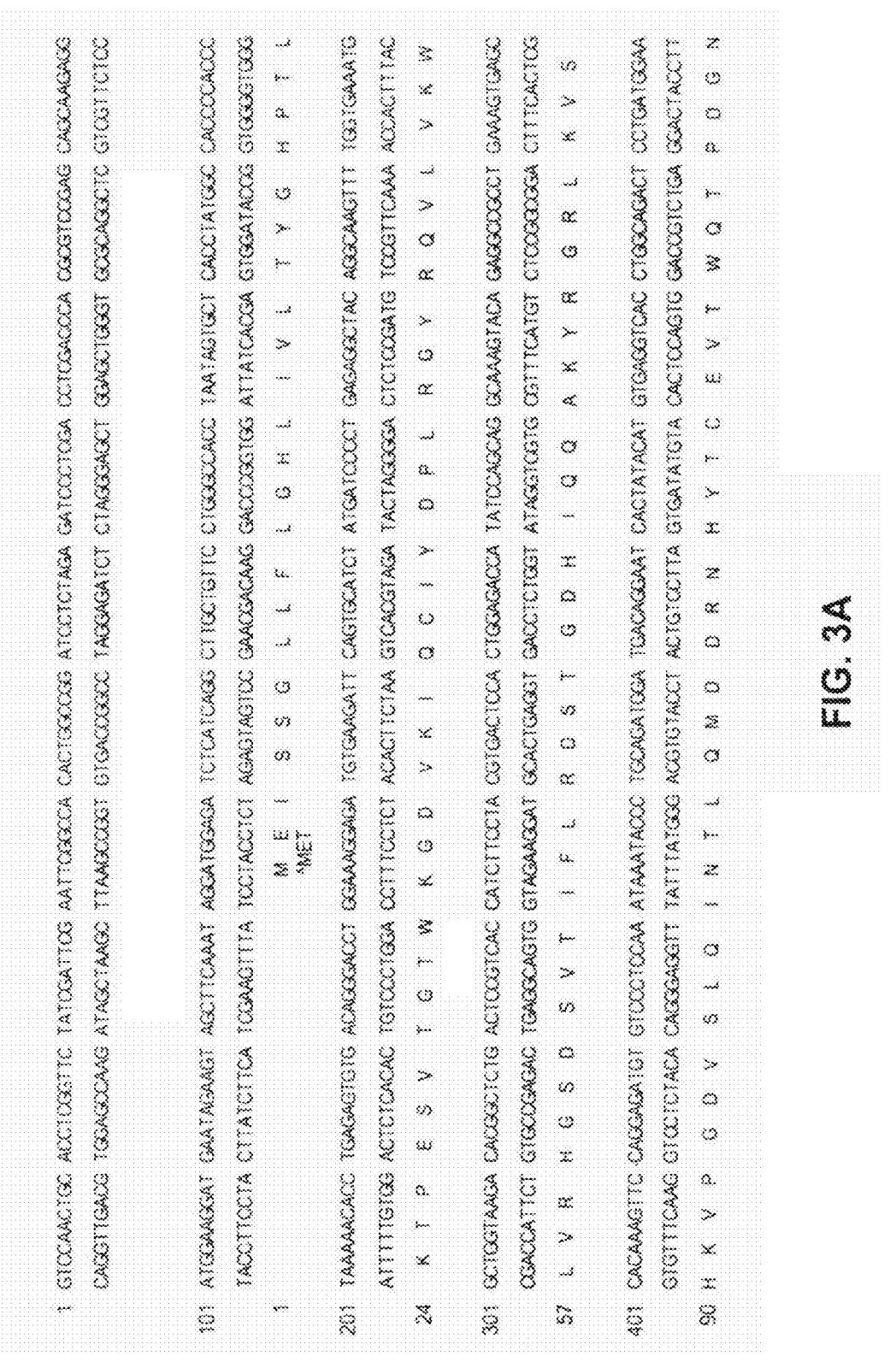
Figure 3B:
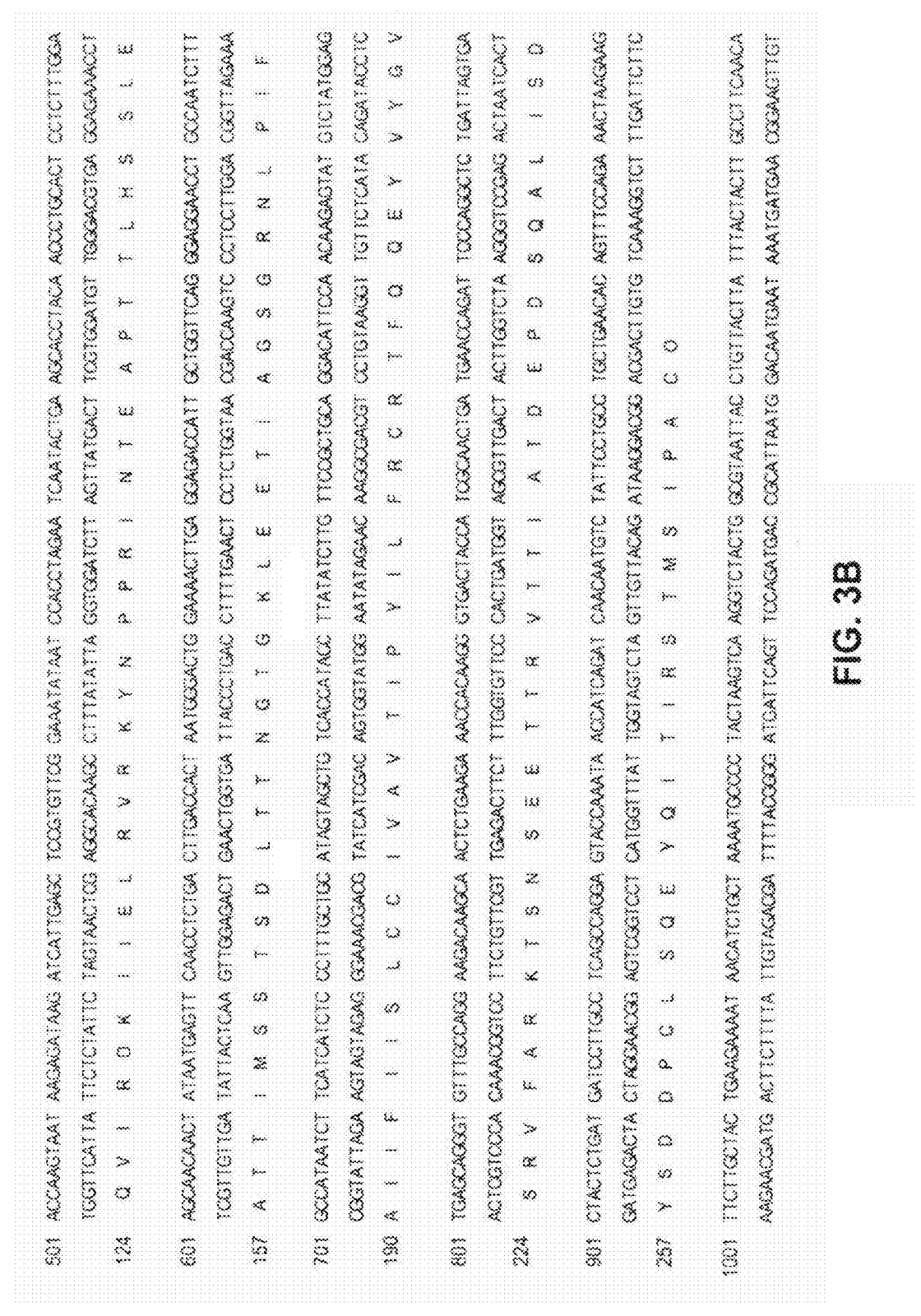

FIG. 3A-3C show the nucleotide and amino acid sequences of the 280-amino acid native murine CRIg (muCRIg, SEQ ID NOS: 5 and 6, respectively).

FIG. 4: Activity of CRIg mutants in binding assay and inhibition assay. Binding affinity for CRIg was measured as competitive displacement of C3b (A), and the biological activity was measured by a hemolysis inhibition assay. PUR10680 was wild-type control (red), RIL41 (blue) and RL41 (green) were two mutants (B). (C) Stepwise optimization of the CRIg binding interface.

Figures 6A, 6B:
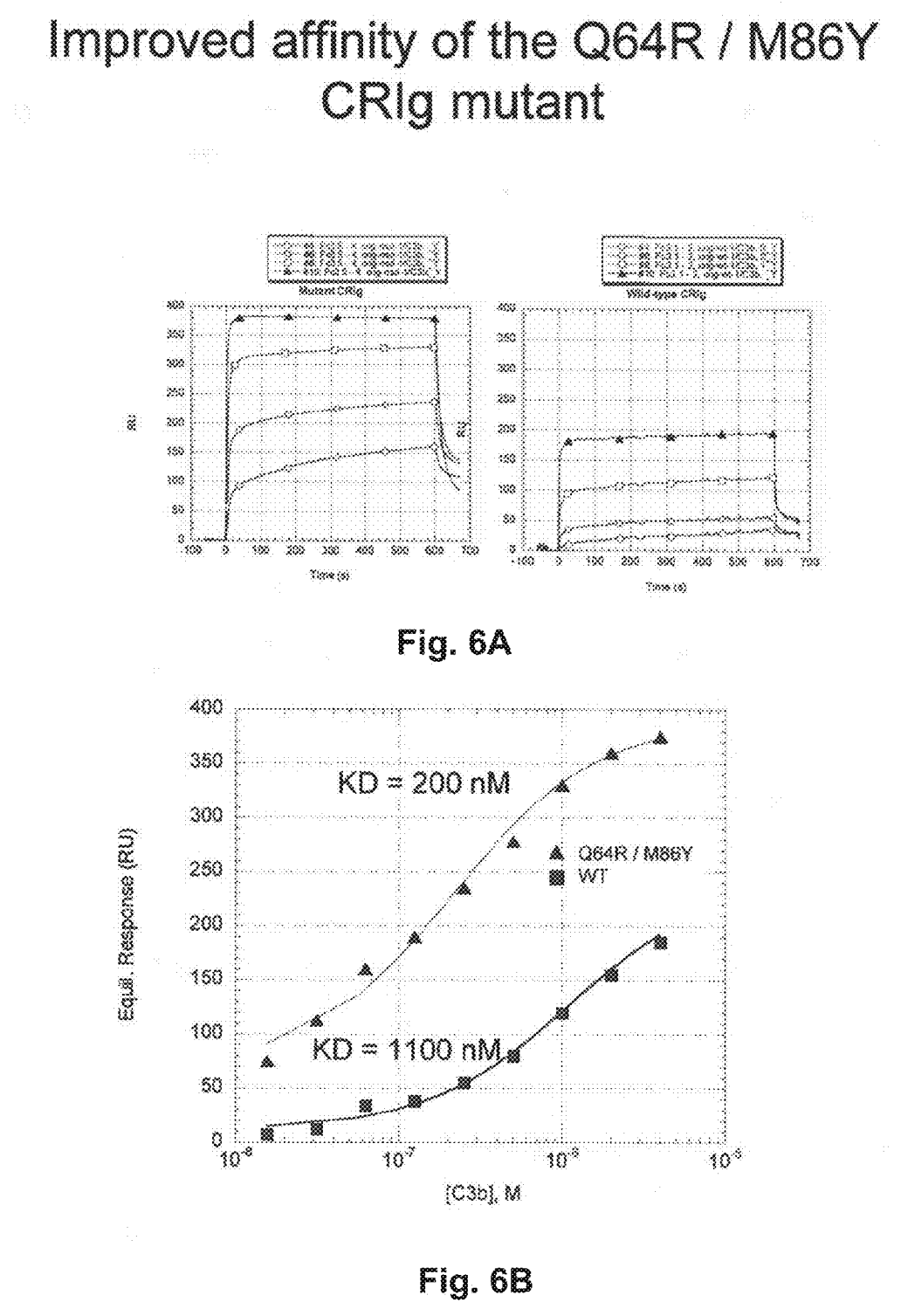

FIG. 6: CRIg mutant Q64R/M86Y shows improved binding affinity by Biacore analysis. (A) SPR sensograms generated by injection of increasing concentrations of C3b over coated CRIg wt and CRIg Q64R M86Y proteins. (B) Steady state analysis of the binding data indicates a Kd of 0.2 micromolar for the Q64R/M86Y mutant and 1.1 micromolar for wild-type CRIg.

(A) Clinical scores of mice injected with KRN serum and treated with various concentrations and versions of wild-type and affinity-matured recombinant human and mouse CRIg proteins. Data represent mean of 4-7 mice per group. (B) Scatter plots of clinical scores from individual mice at day 6 following serum transfer. (C) Hematoxylin and eosin-stained sections of mice treated with CRIg wt of CRIg Q64R M86Y 6 days following serum transfer. (D) Scatter plots of histological scores from mice treated with CRIg wt or CRIg Q64R M86Y 6 days following serum transfer.

FIG. 10: Phage libraries. Five soft-randomized libraries were designed to cover the contact area between CRIg and C3b.

Figure 11:
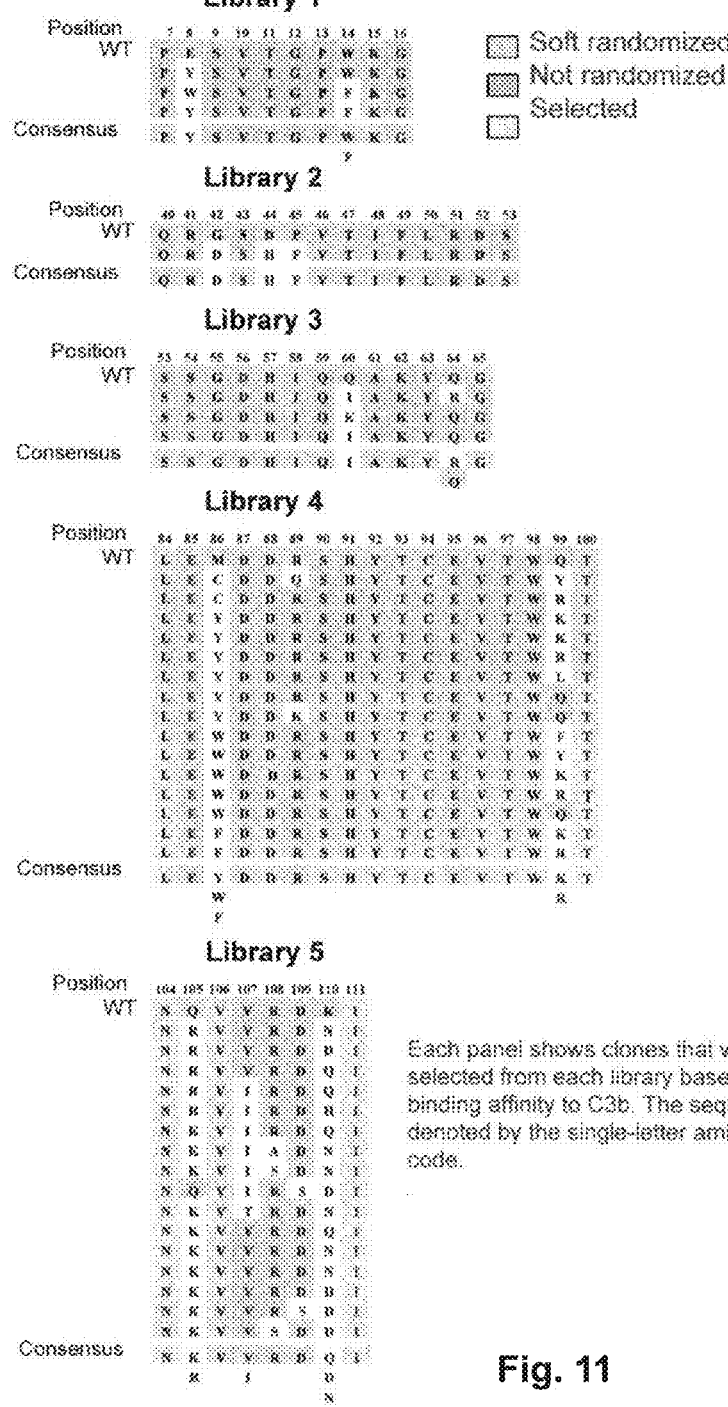

FIG. 11: Step-wise generation of higher affinity CRIg my phage display. Selected mutants of CRIg anti-C3b from the five soft-randomized libraries. Each panel shows clones that were selected from each library based on binding affinity to C3b. The sequence is denoted by the single-letter amino acid code. Each panel compares the individual mutants with the consensus and parent wild-type (WT) sequences. Residues are colored accordingly: blue—soft randomized position; gray—not randomized; yellow—the selected residues, which are different from wild-type (WT). Table 2 discloses SEQ ID NOS 21-63 and 63-67, respectively, in order of appearance.

FIG. 12: Comparison of binding affinities, determined by competitive ELISA, and in vivo hemolysis inhibition for selected mutants. Mutants with a greater than 5 fold increased in binding affinity or in vivo potency are shaded yellow.

FIG. 13: Comparison of binding affinity and in vivo hemolysis inhibition for second generation mutants (parent sequences shown in gray). Mutants with a greater than 5 fold increase over the parent mutant in binding affinity are highlighted in blue, mutants with a greater than 90 fold increase in binding affinity are highlighted in yellow. Similarly, mutants with greater in vivo potency than parent sequences are highlighted in orange.

DETAILED DESCRIPTION OF THE INVENTION

I. Definitions

The terms "CRIg," "PRO362," "JAM4," and "STIgMA" are used interchangeably, and refer to native sequence and variant CRIg polypeptides.

A "native sequence" CRIg, is a polypeptide having the same amino acid sequence as a CRIg polypeptide derived from nature, regardless of its mode of preparation. Thus, native sequence CRIg can be isolated from nature or can be produced by recombinant and/or synthetic means. The term "native sequence CRIg", specifically encompasses naturally-occurring truncated or secreted forms of CRIg (e.g., an extracellular domain sequence), naturally-occurring variant forms (e.g., alternatively spliced forms) and naturally-occurring allelic variants of CRIg.

Native sequence CRIg polypeptides specifically include the full-length 399 amino acids long human CRIg polypeptide of SEQ ID NO: 2 (huCRIg, shown in FIGS. 1A and 1B), with or without an N-terminal signal sequence, with or without the initiating methionine at position 1, and with or without any or all of the transmembrane domain at about amino acid positions 277 to 307 of SEQ ID NO: 2. In a further embodiment, the native sequence CRIg polypeptide is the 305-amino acid, short form of human CRIg (huCRIg-short, SEQ ID NO: 4, shown in FIGS. 2A and 2B), with or without an N-terminal signal sequence, with or without the initiating methionine at position 1, and with or without any or all of the transmembrane domain at about positions 183 to 213 of SEQ ID NO: 4. In a different embodiment, the native sequence CRIg polypeptide is a 280 amino acids long, full-length murine CRIg polypeptide of SEQ ID NO: 6 (muCRIg, shown in FIGS. 3A-3C), with or without an N-terminal signal sequence, with or without the initiating methionine at position 1, and with or without any or all of the transmembrane domain at about amino acid positions 181 to 211 of SEQ ID NO: 6. CRIg polypeptides of other non-human animals, including higher primates and mammals, are specifically included within this definition.

The CRIg "extracellular domain" or "ECD" refers to a form of the CRIg polypeptide, which is essentially free of the transmembrane and cytoplasmic domains of the respective full length molecules. Ordinarily, the CRIg ECD will have less than 1% of such transmembrane and/or cytoplasmic domains and preferably, will have less than 0.5% of such domains. CRIg ECD may comprise amino acid residues 1 or about 21 to X of SEQ ID NO: 2, 4, or 6, where X is any amino acid from about 271 to 281 in SEQ ID NO: 2, any amino acid from about 178 to 186 in SEQ ID NO: 4, and any amino acid from about 176 to 184 in SEQ ID NO: 6.

The term "CRIg variant," as used herein, means an active CRIg polypeptide as defined below having at least about 80% amino acid sequence identity to a native sequence CRIg polypeptide, including, without limitation, the full-length huCRIg (SEQ ID NO: 2), huCRIg-short (SEQ ID NO: 4), and muCRIg (SEQ ID NO: 6), each with or without the N-terminal initiating methionine, with or without the N-terminal signal sequence, with or without all or part of the transmembrane domain and with or without the intracellular domain. In a particular embodiment, the CRIg variant has at least about 80% amino acid sequence homology with the mature, full-length polypeptide from within the sequence of the sequence of SEQ ID NO: 2. In another embodiment, the CRIg variant has at least about 80% amino acid sequence homology with the mature, full-length polypeptide from within the sequence of SEQ ID NO: 4. In yet another embodiment, the CRIg variant has at least about 80% amino acid sequence homology with the mature, full-length polypeptide from within the sequence of SEQ ID NO: 6. Ordinarily, a CRIg variant will have at least about 80% amino acid sequence identity, or at least about 85% amino acid sequence identity, or at least about 90% amino acid sequence identity, or at least about 95% amino acid sequence identity, or at least about 98% amino acid sequence identity, or at least about 99% amino acid sequence identity with the mature amino acid sequence from within SEQ ID NO: 2, 4, or 6. Throughout the description, including the examples, the term "wild-type" or "WT" refers to the mature full-length short form of human CRIg (CRIg(S)) (SEQ ID NO: 4), and the numbering of amino acid residues in the CRIg variants refers to the sequence of the mature sequence within SEQ ID NO: 4, presented as SEQ ID NO: 68.

The CRIg variants of the present invention are CRIg agonists, as hereinafter defined. In particular, the CRIg variants herein maintain selective binding to C3b over C3, where "selective binding" is used to refer to binding to C3b and a lack of binding to C3. In addition, in a preferred embodiment, the CRIg variants of the present invention have increased binding affinity to C3b relative to a native sequence CRIg polypeptide, such as the human long form of CRIg (SEQ ID NO: 2). In various embodiments, the increase in binding affinity is at least about 2 fold, or at least about 3 fold, or at least about 4 fold, or at least about 5 fold, or at least about 6 fold, or at least about 7 fold, or at least about 8 fold, or at least about 9 fold, or at least about 10 fold, or at least about 15 fold, or at least about 20 fold, or at least about 25 fold, or at least about 30 fold, or at least about 35 fold, or at least about 40 fold, or at least about 45 fold, or at least about 50 fold, or at least about 55 fold, or at least about 60 fold, or at least about 65 fold, or at least about 70 fold, or at least about 75 fold, or at least about 80 fold, or at least about 85 fold, or at least about 90 fold, or at least about 95 fold, or at least about 100 fold, relative to the native sequence human CRIg polypeptide of SEQ ID NO: 2. In other embodiments, the increase in binding affinity to C3b relative to the native sequence human CRIg polypeptide of SEQ ID NO: 2 is about 5-10 fold, or about 5-15 fold, or about 5-20 fold, or about 5-25 fold, or about 5-25 fold, or about 5-30 fold, or about 5-35 fold, or about 5-40 fold, or about 5-45 fold, or about 5-50 fold, or about 5-55 fold, or about 5-60 fold, or about 5-65 fold, or about 5-70 fold, or about 5-75 fold, or about 5-80 fold, or about 5-85 fold, or about 5-90 fold, or about 5-95 fold, or about 5-100 fold.

"Percent (%) amino acid sequence identity" with respect to the CRIg variants herein is defined as the percentage of amino acid residues in a CRIg variant sequence that are identical with the amino acid residues in the native CRIg sequence to which they are compared, after aligning the sequences and introducing gaps, if necessary, to achieve the maximum percent sequence identity, and not considering any conservative substitutions as part of the sequence identity. For sequences that differ in length, percent sequence identity is determined relative to the longer sequence, along the full length of the longer sequences. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Sequence identity is then calculated relative to the longer sequence, i.e. even if a shorter sequence shows 100% sequence identity with a portion of a longer sequence, the overall sequence identity will be less than 100%.

"Percent (%) nucleic acid sequence identity" with respect to the CRIg variant encoding sequences identified herein is defined as the percentage of nucleotides in a candidate sequence that are identical with the nucleotides in the CRIg variant encoding sequence, respectively, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Sequence identity is then calculated relative to the longer sequence, i.e. even if a shorter sequence shows 100% sequence identity with a portion of a longer sequence, the overall sequence identity will be less than 100%.

Included in the definition of a CRIg variant are all amino acid sequence variants, as hereinabove defined, regardless of their mode of identification or preparation. Specifically included herein are variants that have been modified by substitution, chemically, enzymatically, or by other appropriate means with a moiety other than a naturally occurring amino acid, as long as they retain a qualitative biological property of a native sequence CRIg. Exemplary non-naturally occurring amino acid substitution include those described herein below.

Amino acid residues are classified into four major groups:

Acidic: The residue has a negative charge due to loss of H ion at physiological pH and the residue is attracted by aqueous solution so as to seek the surface positions in the conformation of a peptide in which it is contained when the peptide is in aqueous solution.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/non-polar: The residues are not charged at physiological pH and the residue is repelled by aqueous solution so as to seek the inner positions in the conformation of a peptide in which it is contained when the peptide is in aqueous medium. These residues are also designated "hydrophobic residues."

Neutral/polar: The residues are not charged at physiological pH, but the residue is attracted by aqueous solution so as to seek the outer positions in the conformation of a peptide in which it is contained when the peptide is in aqueous medium.

Amino acid residues can be further classified as cyclic or non-cyclic, aromatic or non aromatic with respect to their side chain groups these designations being commonplace to the skilled artisan.

Commonly encountered amino acids which are not encoded by the genetic code, include 2-amino adipic acid (Aad) for Glu and Asp; 2-aminopimelic acid (Apm) for Glu and Asp; 2-aminobutyric (Abu) acid for Met, Leu, and other aliphatic amino acids; 2-aminoheptanoic acid (Ahe) for Met, Leu and other aliphatic amino acids; 2-aminoisobutyric acid (Aib) for Gly; cyclohexylalanine (Cha) for Val, and Leu and Ile; homoarginine (Har) for Arg and Lys; 2,3-diaminopropionic acid (Dpr) for Lys, Arg and His; N-ethylglycine (EtGly) for Gly, Pro, and Ala; N-ethylglycine (EtGly) for Gly, Pro, and Ala; N-ethylasparigine (EtAsn) for Asn, and Gln; Hydroxyllysine (Hyl) for Lys; allohydroxyllysine (AHyl) for Lys; 3-(and 4)hydoxyproline (3Hyp, 4Hyp) for Pro, Ser, and Thr; allo-isoleucine (AIle) for Ile, Leu, and Val; .rho.-amidinophenylalanine for Ala; N-methylglycine (MeGly, sarcosine) for Gly, Pro, and Ala; N-methylisoleucine (MeIle) for Ile; Norvaline (Nva) for Met and other aliphatic amino acids; Norleucine (Nle) for Met and other aliphatic amino acids; Ornithine (Orn) for Lys, Arg and His; Citrulline (Cit) and methionine sulfoxide (MSO) for Thr, Asn and Gln; N-methylphenylalanine (MePhe), trimethylphenylalanine, halo (F, Cl, Br, and I)phenylalanine, triflourylphenylalanine, for Phe.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented.

"Ameliorate" as used herein, is defined herein as to make better or improve.

The term "mammal" as used herein refers to any animal classified as a mammal, including, without limitation, humans, non-human primates, domestic and farm animals, and zoo, sports or pet animals such horses, pigs, cattle, dogs, cats and ferrets, etc. In a preferred embodiment of the invention, the mammal is a higher primate, most preferably human.

The term "complement-associated disease" is used herein in the broadest sense and includes all diseases and pathological conditions the pathogenesis of which involves abnormalities of the activation of the complement system, such as, for example, complement deficiencies. The term specifically include diseases and pathological conditions that benefit from the inhibition of C3 convertase. The term additionally includes diseases and pathological conditions that benefit from inhibition, including selective inhibition, of the alternative complement pathway. Complement-associated diseases include, without limitation, inflammatory diseases and autoimmune diseases, such as, for example, rheumatoid arthritis (RA), acute respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulemia, antiphospholipid syndrome, age-related macular degeneration, uveitis, diabetic retinopathy, allo-transplantation, hyperacute rejection, hemodialysis, chronic occlusive pulmonary distress syndrome (COPD), asthma, and aspiration pneumonia. In a preferred embodiment, the "complement-associated disease" is a disease in which the alternative pathway of complement plays a prominent role, including rheumatoid arthritis (RA), complement-associated eye conditions, such as age-related macular degeneration, anti-phospholipid syndrome, intestinal and renal ischemia-reperfusion injury, and type II membranoproliferative glomerulonephritis.

The term "complement-associated eye condition" is used herein in the broadest sense and includes all eye conditions and diseases the pathology of which involves complement, including the classical and the alternative pathways, and in particular the alternative pathway of complement. Specifically included within this group are all eye conditions and diseases the associated with the alternative pathway, the occurrence, development, or progression of which can be controlled by the inhibition of the alternative pathway. Complement-associated eye conditions include, without limitation, macular degenerative diseases, such as all stages of age-related macular degeneration (AMD), including dry and wet (non-exudative and exudative) forms, choroidal neovascularization (CNV), uveitis, diabetic and other ischemia-related retinopathies, endophthalmitis, and other intraocular neovascular diseases, such as diabetic macular edema, pathological myopia, von Hippel-Lindau disease, histoplasmosis of the eye, Central Retinal Vein Occlusion (CRVO), corneal neovascularization, and retinal neovascularization. A preferred group of complement-associated eye conditions includes age-related macular degeneration (AMD), including non-exudative (wet) and exudative (dry or atrophic) AMD, choroidal neovascularization (CNV), diabetic retinopathy (DR), and endophthalmitis.

The term "inflammatory disease" and "inflammatory disorder" are used interchangeably and mean a disease or disorder in which a component of the immune system of a mammal causes, mediates or otherwise contributes to an inflammatory response contributing to morbidity in the mammal. Also included are diseases in which reduction of the inflammatory response has an ameliorative effect on progression of the disease. Included within this term are immune-mediated inflammatory diseases, including autoimmune diseases.

The term "T-cell mediated" disease means a disease in which T cells directly or indirectly mediate or otherwise contribute to morbidity in a mammal. The T cell mediated disease may be associated with cell mediated effects, lymphokine mediated effects, etc. and even effects associated with B cells if the B cells are stimulated, for example, by the lymphokines secreted by T cells.

Examples of immune-related and inflammatory diseases, some of which are T cell mediated, include, without limitation, inflammatory bowel disease (IBD), systemic lupus erythematosus, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vaculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic polyneuropathy, hepatobiliary diseases such as infectious hepatitis (hepatitis A, B, C, D, E and other nonhepatotropic viruses), autoimmune chronic active hepatitis, primary biliary cirrhosis, granulomatous hepatitis, and sclerosing cholangitis, inflammatory and fibrotic lung diseases (e.g., cystic fibrosis), gluten-sensitive enteropathy, Whipple's disease, autoimmune or immune-mediated skin diseases including bullous skin diseases, erythema multiforme and contact dermatitis, psoriasis, allergic diseases of the lung such as eosinophilic pneumonia, idiopathic pulmonary fibrosis and hypersensitivity pneumonitis, transplantation associated diseases including graft rejection, graft-versus host disease, Alzheimer's disease, and atherosclerosis.

Administration "in combination with" one or more further therapeutic agents includes simultaneous (concurrent) and consecutive administration in any order.

"Active" or "activity" in the context of variants of the CRIg polypeptides of the invention refers to form(s) of such polypeptides which retain the biological and/or immunological activities of a native or naturally-occurring polypeptide of the invention. A preferred biological activity is the ability to bind C3b, and/or to affect complement or complement activation, in particular to inhibit the alternative complement pathway and/or C3 convertase. Inhibition of C3 convertase can, for example, be measured by measuring the inhibition of C3 turnover in normal serum during collagen- or antibody-induced arthritis, or inhibition of C3 deposition is arthritic joints. "Biological activity" in the context of a polypeptide that mimics CRIg biological activity refers, in part, to the ability of such molecules to bind C3b and/or to affect complement or complement activation, in particular, to inhibit the alternative complement pathway and/or C3 convertase.

The term CRIg "agonist" is used in the broadest sense, and includes any molecule that mimics a qualitative biological activity (as hereinabove defined) of a native sequence CRIg polypeptide.

"Operably linked" refers to juxtaposition such that the normal function of the components can be performed. Thus, a coding sequence "operably linked" to control sequences refers to a configuration wherein the coding sequence can be expressed under the control of these sequences and wherein the DNA sequences being linked are contiguous and, in the case of a secretory leader, contiguous and in reading phase. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Linking is accomplished by ligation at convenient restriction sites. If such sites do not exist, then synthetic oligonucleotide adaptors or linkers are used in accord with conventional practice.

"Control sequences" refer to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may then also be integrated into the host chromosome.

As used herein, "cell," "cell line," and "cell culture" are used interchangeably and all such designations include progeny. Thus, "transformants" or "transformed cells" includes the primary subject cell and cultures derived therefrom without regard for the number of transfers. It is also understood that all progeny may not be precisely identical in DNA content because deliberate or inadvertent mutations may occur. Mutant progeny that have the same functionality as screened for in the originally transformed cell are included. Where distinct designations are intended, it will be clear from the context.

"Plasmids" are designated by a lower case "p" preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

A "phage display library" is a protein expression library that expresses a collection of cloned protein sequences as fusions with a phage coat protein. Thus, the phrase "phage display library" refers herein to a collection of phage (e.g., filamentous phage) wherein the phage express an external (typically heterologous) protein. The external protein is free to. interact with (bind to) other moieties with which the phage are contacted. Each phage displaying an external protein is a "member" of the phage display library.

The term "filamentous phage" refers to a viral particle capable of displaying a heterogenous polypeptide on its surface, and includes, without limitation, f1, fd, Pf1, and M13. The filamentous phage may contain a selectable marker such as tetracycline (e.g., "fd-tet"). Various filamentous phage display systems are well known to those of skill in the art (see, e.g., Zacher et al., Gene, 9:127-140 (1980), Smith et al., Science, 228:1315-1317 (1985); and Parmley and Smith, Gene, 73:305-318 (1988)).

The term "panning" is used to refer to the multiple rounds of screening process in identification and isolation of phages carrying compounds, such as antibodies, with high affinity and specificity to a target.

The phrase "conserved amino acid residues" is used to refer to amino acid residues that are identical between two or more amino acid sequences aligned with each other.

II. Detailed Description

Complement is an important component of the innate and adaptive immune response, yet complement split products generated through activation of each of the three complement pathways (classical, alternative, and lectin) can cause inflammation and tissue destruction. Thus, uncontrolled complement activation due to the lack of appropriate complement regulation has been associated with various chronic inflammatory diseases. Dominant in this inflammatory cascade are the complement split products C3a and C5a that function as chemoattractant and activators of neutrophils and inflammatory macrophages via the C3a and C5a receptors (Mollnes, T. E., W. C. Song, and J. D. Lambris. 2002. Complement in inflammatory tissue damage and disease. *Trends Immunol.* 23:61-64.

CRIg is a recently discovered complement receptor, which is expressed on a subpopulation of tissue resident macrophages. As a functional receptor, the extracellular IgV domain of CRIg is a selective inhibitor of the alternative pathway of complement (Wiesmann et al., Nature, 444(7116):217-20, 2006). A soluble form of CRIg has been shown to reverse inflammation and bone loss in experimental models of arthritis by inhibiting the alternative pathway of complement in the joint. It has also been shown that the alternative pathway of complement is not only required for disease induction, but also disease progression. Thus, inhibition of the alternative pathway by CRIg constitutes a promising therapeutic avenue for the prevention and treatment of diseases and disorders the pathogenesis of which involves the alternative pathway of complement. For further details see, e.g. Helmy et al., Cell, 125(1):29-32 2006) and Katschke et al., J. Exp Med 204(6): 1319-1325 (2007).

However, CRIg affinity for the convertase subunit C3b is low (micromolar range). In order to generate a more potent inhibitor to develop a therapeutic reagent, the crystal structure of CRIg in complex with C3b was used as a guide and we employed phage display technology to generate CRIg variants with improved binding affinity for C3b.

Thus, the present invention concerns CRIg variants with improved properties, such as improved binding affinity for C3b and enhanced inhibitory efficacy.

Identification of Affinity Matured CRIg Variants

As described in greater detail in the Example, phage display of protein or peptide libraries offers a useful methodology for the selection of CRIg variants with improved binding affinity for C3b and/or other improved properties, such as enhanced biological activity (Smith, G. P., (1991) Curr. Opin. Biotechnol. 2:668-673). High affinity proteins, displayed in a monovalent fashion as fusions with the M13 gene III coat protein (Clackson, T., (1994) et al., Trends Biotechnol. 12:173-183), can be identified by cloning and sequencing the corresponding DNA packaged in the phagemid particles after a number of rounds of binding selection.

Affinity maturation using phage display has been described, for example, in Lowman et al., Biochemistry 30(45): 10832-10838 (1991), see also Hawkins et al, J. Mol Biol. 254: 889-896 (1992), and in the Example below. While not strictly limited to the following description, this process can be described briefly as: several sites within a predetermined region are mutated to generate all possible amino acid substitutions at each site. The antibody mutants thus generated are displayed in a monovalent fashion from filamentous phage particles as fusions to the gene III product of M13 packaged within each particle. The phage expressing the various mutants can be cycled through rounds of binding selection, followed by isolation and sequencing of those mutants which display high affinity. The method is also described in U.S. Pat. No. 5,750,373, issued May 12, 1998.

A modified procedure involving pooled affinity display is described in Cunningham, B. C. et al, EMBO J. 13(11), 2508-2515 (1994). The method provides a method for selecting novel binding polypeptides comprising: a) constructing a replicable expression vector comprising a first gene encoding a polypeptide, a second gene encoding at least a portion of a natural or wild-type phage coat protein wherein the first and second genes are heterologous, and a transcription regulatory element operably linked to the first and second genes, thereby forming a gene fusion encoding a fusion protein; b) mutating the vector at one or more selected positions within the first gene thereby forming a family of related plasmids; c) transforming suitable host cells with the plasmids; d) infecting the transformed host cells with a helper phage having a gene encoding the phage coat protein; e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle; f) contacting the phagemid particles with a target molecule so that at least a portion of the phagemid particles bind to the target molecule; and g) separating the phagemid particles that bind from those that do not. Preferably, the method further comprises transforming suitable host cells with recombinant phagemid particles that bind to the target molecule and repeating steps d) through g) one or more times.

It is noted that, while the CRIg variants of the present invention have been identified using phage display, other techniques and other display techniques can also be used to identify CRIg variants with improved properties, including affinity matured CRIg variants.

The affinity matured CRIg variants of the present invention were designed to cover the contact area between CRIg and C3b, which was identified using the crystal structure of a CRIg and C3b:CRIg complex disclosed in U.S. application publication no. 20080045697. I particular, as shown in FIG. 11, libraries 1-5 were designed to cover residues E8-K15, R41-T47, S54-Q64, E85-Q99, and Q105-K111, respectively, of the native sequence full-length CRIg molecule of SEQ ID NO: 2.

In one embodiment, the CRIg variants herein contain an amino acid substitution at one or more amino acid positions selected from the group consisting of positions 8, 14, 18, 42, 44, 45, 60, 64, 86, 99, 105, and 110 in the amino acid sequence of SEQ ID NO: 2.

Representative CRIg variants herein are set forth in FIG. 12.

Preferably, the substitution is at one or more of amino acid positions 60, 64, 86, 99, 105 and 110 of the amino acid sequence of full-length native CRIg of SEQ ID NO: 2.

Without limitation, affinity matured CRIg variants specifically include one or more of the following substitutions within the SEQ ID NO: 2: E8W, W14F, E84Y/W14F; P45F; G42D/D44H/P45F; Q60I; Q64R; Q60I/Q64R; M86Y; M86W, M86F, M86W/Q9R; M86F/Q99R; K110D, K11N; Q105R/K110N; Q105R/K110Q; Q105K/K110D.

Further variants of native sequence CRIg of SEQ ID NO: 2 with two or more amino acid substitutions are shown in FIG. 12. Specifically included within this group are Q64R/M86Y; Q60I/Q64R/E8Y; Q60I/Q64R/G42D; Q60I/Q64R/P45F; Q60I/Q64R/G42D/D44H/P45F; Q60I/Q64R/M86Y; Q60I/Q64R/Q105R; Q60I/Q64R/Q105K; Q60I/Q64R/K110N; Q60I/Q105R/K110N; M86Y/E8Y; M86Y/G42D/D44H/P45F; M86Y/P45F; M86Y/G42D/D44H/P45F; M86Y/Q99K; M86Y/Q99R; M86Y/Q105R; M86Y/Q105K; and M86Y/Q105R/K110N.

Preferred CRIg variants herein comprise a mutation selected from the group consisting of: Q60I; Q64R; Q60I/Q64R; M86Y; Q99L; Q105K/K110D; E8W/Q105R/K110N; Q64R/M86Y; Q60I/Q64R/E8Y; Q60I/Q64R/G42D; Q60I/Q64R/P45F; Q60I/Q64R/G42D/D44H/P45F; Q60I/Q64R/M86Y; Q60I/Q64R/Q105R; Q60I/Q64R/Q105K; Q60I/Q64R/K110N; M86Y/P45F; M86Y/Q105K.

Particularly preferred variants comprise the mutations Q60I/Q64R/M86Y or Q60I/Q64R/G42D/D44H/P45F.

Figure 13:
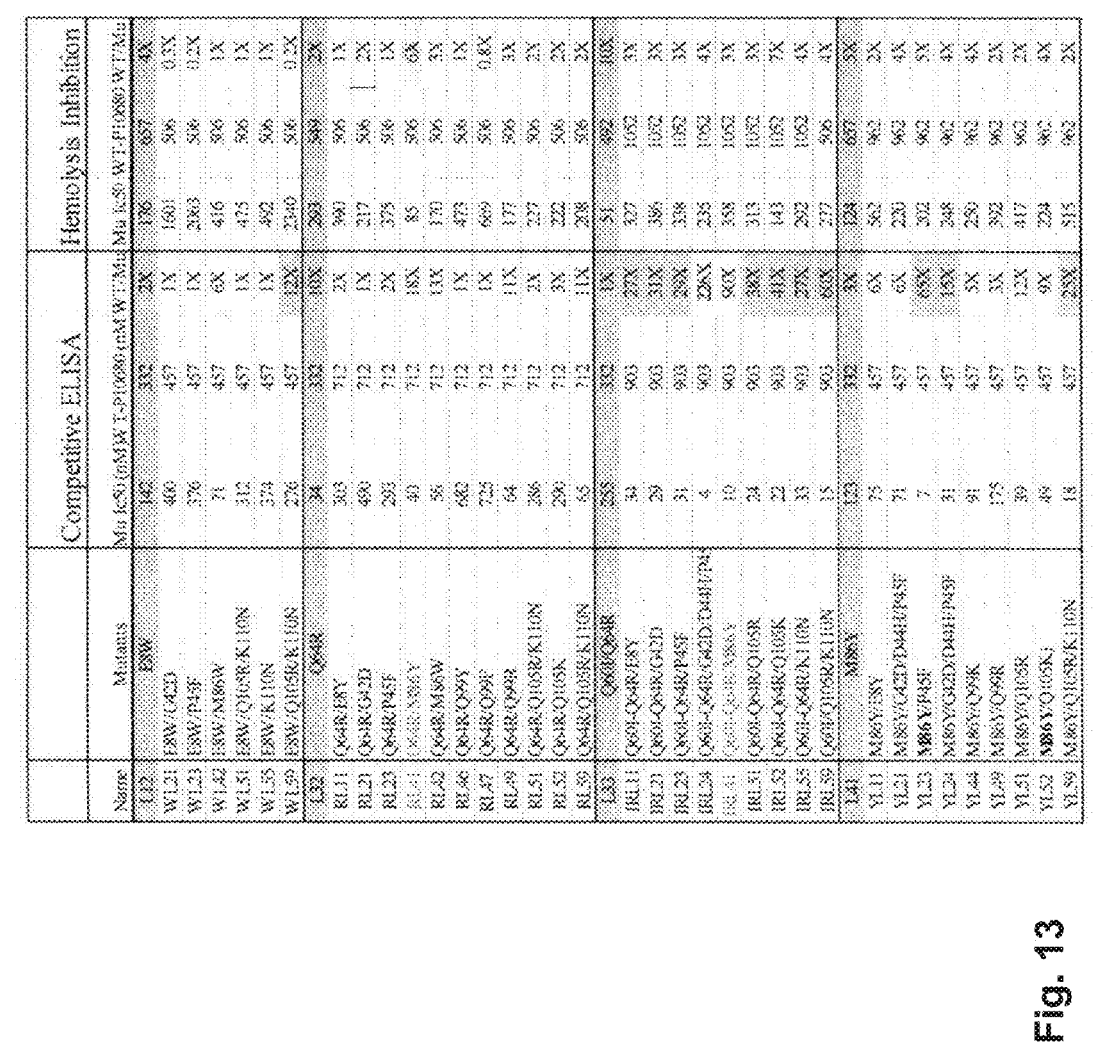

Variants which contain one or more of the mutations listed above or in FIGS. 12 and 13 but otherwise retain the native CRIg sequence of SEQ ID NO: 2 are specifically included herein. Such variants will be designated herein by listing the particular mutation followed by "CRIg." Thus for example, a variant which differs from native sequence CRIg of SEQ ID NO: 2 only by the mutation E8W will be designated as "E8W CRIg," a variant which differs from native sequence CRIg of SEQ ID NO: 2 only by the mutations Q60I/Q64R/M86Y will be designated as "Q60I/Q64R/M86Y CRIg," etc.

Preparation of CRIg Variants

Various techniques are available which may be employed to produce DNA, which can encode proteins for the recombinant synthesis of the CRIg variants of the invention. For instance, it is possible to derive DNA based on naturally occurring DNA sequences that encode for changes in an amino acid sequence of the resultant protein. These mutant DNA can be used to obtain the CRIg variants of the present invention. These techniques contemplate, in simplified form, obtaining a gene encoding a native CRIg polypeptide, modifying the genes by recombinant techniques such as those discussed below, inserting the genes into an appropriate expression vector, inserting the vector into an appropriate host cell, culturing the host cell to cause expression of the desired CRIg variant, and purifying the molecule produced thereby.

Somewhat more particularly, a DNA sequence encoding a CRIg variant of the present invention is obtained by synthetic construction of the DNA sequence as described in standard textbooks, such as, for example, Sambrook, J. et al., Molecular Cloning (2nd ed.), Cold Spring Harbor Laboratory, N.Y., (1989).

a. Oligonucleotide-Mediated Mutagenesis

Oligonucleotide-mediated mutagenesis is the preferred method for preparing substitution, deletion, and insertion variants of a native CRIg polypeptide or a fragment thereof. This technique is well known in the art as described by Zoller et al., Nucleic Acids Res. 10: 6487-6504 (1987). Briefly, nucleic acid encoding the starting polypeptide sequence is altered by hybridizing an oligonucleotide encoding the desired mutation to a DNA template, where the template is the single-stranded form of the plasmid containing the unaltered or native DNA sequence of encoding nucleic acid. After hybridization, a DNA polymerase is used to synthesize an entire second complementary strand of the template which will thus incorporate the oligonucleotide primer, and will code for the selected alteration of starting nucleic acid.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., Proc. Natl. Acad Sci. USA 75: 5765 (1978).

If phage display is used, the DNA template can only be generated by those vectors that are either derived from bacteriophage M13 vectors (the commonly available M13 mp 18 and M13 mp19 vectors are suitable), or those vectors that contain a single-stranded phage origin or replication as described by Viera et al., Meth. Enzymol. 153:3 (1987). Thus, the DNA that is to be mutated must be inserted into one of these vectors in order to generate a single-stranded template. Production of the single-stranded template is described in sections 4.21-4.41 of Sambrook et al., supra.

To alter the native DNA sequence, the oligonucleotide is hybridized to the single stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of CRIg, and the other strand (the original template) encodes the native, unaltered sequence of CRIg. This heteroduplex molecule is then transformed into a suitable host cell, usually a prokaryote such as E. coli JM-101. After growing the cells, they are plated onto agarose plates and screened using the oligonucleotide primer radiolabelled with $^{32}$Phosphate to identify the bacterial colonies that contain the mutated DNA.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli JM101, as described above.

Mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one or two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant. The first round is as described for the single mutants: wild-type DNA is used for the template, and oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

b. Cassette Mutagenesis

This method is also a preferred method for preparing substitution, deletion, and insertion variants of CRIg. The method is based on that described by Wells et al. Gene 34: 315 (1985). The starting material is the plasmid (or other vector) comprising gene 1, the gene to be mutated. The codon(s) to be mutated in the nucleic acid encoding the starting CRIg molecule are identified. There must be a unique restriction endonuclease site on each side of the identified mutation site(s). If no such restriction sites exist, they may be generated using the above-described oligonucleotide-mediated mutagenesis method to introduce them at appropriate locations in gene 1. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated DNA sequence of CRIg.

c. Recombinant Production of CRIG Variants

The DNA encoding variants are then inserted into an appropriate plasmid or vector. The vector is used to transform a host cell. In general, plasmid vectors containing replication and control sequences which are derived from species compatible with the host cell are used in connection with those hosts. The vector ordinarily carries a replication site, as well as sequences which encode proteins that are capable of providing phenotypic selection in transformed cells.

For example, E. Coli may be transformed using pBR322, a plasmid derived from an E. coli species (Mandel, M. et al., (1970) J. Mol. Biol. 53:154). Plasmid pBR322 contains genes for ampicillin and tetracycline resistance, and thus provides easy means for selection. Other vectors include different features such as different promoters, which are often important in expression. For example, plasmids pKK223-3, pDR720, and pPL-λ, represent expression vectors with the tac, trp, or PL promoters that are currently available (Pharmacia Biotechnology).

Other preferred vectors can be constructed using standard techniques by combining the relevant traits of the vectors described herein. Relevant traits of the vector include the promoter, the ribosome binding site, the variant gene or gene fusion, the signal sequence, the antibiotic resistance markers, the copy number, and the appropriate origins of replication.

Suitable host cells for cloning or expressing the DNA in the vectors herein include prokaryote, yeast, or higher eukaryote cells. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serrafia*, e.g, *Serratia marcescans*, and *Shigeila*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X 1776 (ATCC 31,537), and *E. coil* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. Saccharomyces cerevisiae, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; yarrowia (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa califomica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subloned for growth in suspension culture, Graham et al, J. Gen Virol. 36:59 (1977)); baby hamster kidney cells (BHK, ATCC CCL 10); Chinese hamster ovary cells/–DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for the production of the CRIg variants herein and cultured in conventional nutrient media modified as appropriate for inducing promoters, selecting transformants, or amplifying the genes encoding the desired sequences.

The host cells used to produce the CRIg variants of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the CRIg variant can be produced intracellularly, in the periplasmic space, or directly secreted into the medium. If the CRIg variant is produced intracellularly, as a first step, the particulate debris, either host cells or lysed cells, is removed, for example, by centrifugation or ultrafiltration. Where the CRIg variant is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The CRIg variant prepared from the cells can be purified by known techniques, using, for example, hydroxylapatite chromatography, gel electrophoresis, dialysis, and/or affinity chromatography.

Further Modifications of CRIg Variants

The CRIg variants of the present invention may also be modified in a way to form a chimeric molecule comprising CRIg variant, including fragments thereof, fused to another, heterologous polypeptide or amino acid sequence. In one embodiment, such a chimeric molecule comprises a fusion of CRIg variant, or a fragment thereof, with a tag polypeptide which provides an epitope to which an anti-tag antibody can selectively bind. The epitope tag is generally placed at the amino- or carboxyl-terminus of the variant CRIg polypeptide. The presence of such epitope-tagged forms of the CRIg variant can be detected using an antibody against the tag polypeptide. Also, provision of the epitope tag enables the CRIg polypeptide to be readily purified by affinity purification using an anti-tag antibody or another type of affinity matrix that binds to the epitope tag. Various tag polypeptides and their respective antibodies are well known in the art.

Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et al., Protein Engineering, 3(6):547-553 (1990)). Other tag polypeptides include the Flag-peptide (Hopp et al., BioTechnology, 6:1204-1210 (1988)); the KT3 epitope peptide (Martin et al., Science, 255:192-194 (1992)); an .quadrature.-tubulin epitope peptide [Skinner et al., J. Biol. Chem., 266: 15163-15166 (1991)]; and the T7 gene 10 protein peptide tag (Lutz-Freyermuth et al., Proc. Natl. Acad. Sci. USA, 87:6393-6397 (1990)).

In another embodiment, the chimeric molecule may comprise a fusion of the CRIg variant or a fragment thereof with an immunoglobulin or a particular region of an immunoglobulin. For a bivalent form of the chimeric molecule, such a fusion could be to the Fc region of an IgG molecule. These fusion polypeptides are antibody-like molecules which combine the binding specificity of a heterologous protein (an "adhesin") with the effector functions of immunoglobulin constant domains, and are often referred to as immunoadhesins. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The simplest and most straightforward immunoadhesin design combines the binding region(s) of the "adhesin" protein with the hinge and Fc regions of an immunoglobulin heavy chain. Ordinarily, when preparing the CRIg-immunoglobulin chimeras of the present invention, nucleic acid encoding the extracellular domain of CRIg will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge and CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain.

The precise site at which the fusion is made is not critical; particular sites are well known and may be selected in order to optimize the biological activity, secretion or binding characteristics of the CRIg-immunoglobulin chimeras.

In some embodiments, the CRIg-immunoglobulin chimeras are assembled as monomers, or hetero- or homo-multimer, and particularly as dimers or tetramers, essentially as illustrated in WO 91/08298.

In a preferred embodiment, the CRIg extracellular domain sequence is fused to the N-terminus of the C-terminal portion of an antibody (in particular the Fc domain), containing the effector functions of an immunoglobulin, e.g. immunoglobulin G.sub. 1 (IgG 1). It is possible to fuse the entire heavy chain constant region to the CRIg extracellular domain sequence. However, more preferably, a sequence beginning in the hinge region just upstream of the papain cleavage site (which defines IgG Fc chemically; residue 216, taking the first residue of heavy chain constant region to be 114, or analogous sites of other immunoglobulins) is used in the fusion. In a particularly preferred embodiment, the CRIg amino acid sequence is fused to the hinge region and CH2 and CH3, or to the CH1, hinge, CH2 and CH3 domains of an IgG 1, gG2, or IgG3 heavy chain. The precise site at which the fusion is made is not critical, and the optimal site can be determined by routine experimentation.

In some embodiments, the CRIg-immunoglobulin chimeras are assembled as multimer, and particularly as homodimers or -tetramers. Generally, these assembled immunoglobulins will have known unit structures. A basic four chain structural unit is the form in which IgG, IgD, and IgE exist. A four unit is repeated in the higher molecular weight immunoglobulins; IgM generally exists as a pentamer of basic four units held together by disulfide bonds. IgA globulin, and occasionally IgG globulin, may also exist in multimeric form in serum. In the case of multimer, each four unit may be the same or different.

Alternatively, the CRIg extracellular domain sequence can be inserted between immunoglobulin heavy chain and light chain sequences such that an immunoglobulin comprising a chimeric heavy chain is obtained. In this embodiment, the CRIg sequence is fused to the 3' end of an immunoglobulin heavy chain in each arm of an immunoglobulin, either between the hinge and the CH2 domain, or between the CH2 and CH3 domains. Similar constructs have been reported by Hoogenboom et al., Mol. Immunol., 28:1027-1037 (1991).

Although the presence of an immunoglobulin light chain is not required in the immunoadhesins of the present invention, an immunoglobulin light chain might be present either covalently associated to a CRIg-immunoglobulin heavy chain fusion polypeptide, or directly fused to the CRIg extracellular domain. In the former case, DNA encoding an immunoglobulin light chain is typically coexpressed with the DNA encoding the CRIg-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567 issued Mar. 28, 1989.

Pharmaceutical Compositions

The CRIg variants of the present invention can be administered for the treatment of diseases the pathology of which involves the alternative complement pathway.

Therapeutic formulations are prepared for storage by mixing the active molecule having the desired degree of purity with optional pharmaceutically acceptable carriers, excipients or stabilizers (Remington's Pharmaceutical Sciences 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Lipofections or liposomes can also be used to deliver the polypeptide, antibody, or an antibody fragment, into cells. Where antibody fragments are used, the smallest fragment which specifically binds to the binding domain of the target protein is preferred. For example, based upon the variable region sequences of an antibody, peptide molecules can be designed which retain the ability to bind the target protein sequence. Such peptides can be synthesized chemically and/or produced by recombinant DNA technology (see, e.g. Marasco et al., Proc. Nati. Acad. Sci. USA 90, 7889-7893 [1993]).

The formulation herein may also contain more than one active compound as necessary for the particular indication being treated, preferably those with complementary activities that do not adversely affect each other. Such molecules are suitably present in combination in amounts that are effective for the purpose intended.

The active molecules may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(—)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37 C, resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Methods of Treatment

As a result of their ability to inhibit complement activation, in particular the alternative complement pathway, the CRIg variants of the present invention find utility in the prevention and/or treatment of complement-associated diseases and pathological conditions. Such diseases and conditions include, without limitation, complement-associated, inflammatory and autoimmune diseases.

Specific examples of complement-associated, inflammatory and immune related diseases and disorders that can be targeted by the CRIg variants herein have been listed earlier.

Further details of the invention are illustrated by the following non-limiting Examples.

Example 1

Preparation of Affinity Matured CRIg Variants

Materials And Methods

Materials:

Materials—Enzymes and M13-KO7 helper phage (New England Biolabs); Maxisorp immunoplates plates (Nunc. Roskilde, Denmark); 96-well U-bottom Polypropylene plate (COSTAR; Cat. #3365); 96-well flat bottom, non-binding plate (NUNC; Cat. #269626); Horseradish peroxidase/anti-M13 antibody conjugate (Pharmacia); 3,3',5,5'-Tetramethylbenzidine, $H_2O_2$ peroxidase substrate (TEB) (Kirkegaard and Perry Laboratories, Inc); *Escherichia coli* XL1-blue and *E. coli*. BL21(DE3) (Stratagene); Bovine serum albumin (BSA) and Tween 20 (Sigma); Ni-NTA agarose (Qiagen); Rabbit RBC (Colorado Serum Company; Cat. #CS1081); Gelatin Veronal Buffer (GVB) [100 mL Veronal Buffer (Bio Whittaker; Cat. #12-624E); Gelatin (Bovine Skin Type B; SIGMA; Cat. #G9391-100G); C1q-depleted Serum (CompTech; Cat. #A300); fH Protein (Complement Technology; Cat. #A137); Anti-FLAG-HRP, mAb in 50% glycerol, Sigma Cat#A-8592 1.1 mg/mL Construction of Phage-Display CRIg Libraries A DNA fragment encoding CRIg was ligated into a XhoI and SpeI-digested phagemid vector (p3DvlzPDZ-gD) (Kunkel et al., Methods Enzymol. 154:367-382 (1987)) as wild type control and template for design CRIg variants. Then, templates with the TAA stop codon at each residue targeted for randomization were prepared from CJ239 *E. coli* cells (Kunkel et al., 1987, supra). A soft randomization strategy was used for CRIg variants selection, in which a mutation rate of approximately 50% was introduced at selected position by using a poisoned oligonucletide strategy with 70-10-10-10 mixtures of bases favoring the wild-type nucleotides. In the libraries design: 5=50% A, 10% G, 10% C and 10% T; 6=50% G, 10% A, 10% C and 10% T; 7=50% C, 10% A, 10% G and 10% T; 8=50% T, 10% A, 10% G and 10% C.

Five libraries have been designed.

```
BCR1,                                           (SEQ ID NO: 7)
ATC CTG GAA GTG CAA 656

(SEQ ID NO: 8)
AGT GTA ACA GGA CCT 866

(SEQ ID NO: 9)
555 GGG GAT GTG AAT CTT
in library 1;
```

-continued

BCR2, (SEQ ID NO: 10)
AAG TGG CTG GTA CAA 768

(SEQ ID NO: 11)
668 TCA 657 775 688 577 ATC TTT (SEQ ID NO: 12)
786 CGT 657 TCT TCT GGA GAC CAT
in library 2;

BCR3, (SEQ ID NO: 13)
TTT CTA CGT GAC TCT (SEQ ID NO: 14)
877 668 657 757 588 756 756 678 555 TAC 756 GGC

CGC CTG CAT GTVG in library 3;

BCR4, (SEQ ID NO: 15)
CAA TTG AGC ACC CTG (SEQ ID NO: 16)
656 586 657 GAC 768 AGC CAC TAC ACG TGT 656

(SEQ ID NO: 17)
GTC ACC TGG 756

(SEQ ID NO: 18)
ACT CCT GAT GGC AAC in library 4;

BCR5, (SEQ ID NO: 19)
ACT CCT GAT GGC AAC 756

(SEQ ID NO: 20)
GTC 688 768 657 555 ATT ACT GAG CTC CGT in library 5.

Side-directed mutagenesis for the point mutations was carried out as above by using appropriated codons to produce the respective mutations, and the correct clones were confirmed by sequence.

Library Sorting and Screening to Select CRIg Variants:

Maxisorp immunoplates were coated overnight at 4° C. with C3b (5 µg/ml) and blocked for 1 hr at room temperature with phosphate-buffered saline (PBS) and 0.05% (w/v) bovine serum albumin (BSA). Phage libraries were added to the C3b coated plates and incubated at room temperature for 3 hr. The plates were washed ten times and bound phage were eluted with 50 mM HCl and neutralized with equal volume of 1.0 M Tris base (pH7.5). Recovered phages were amplified by passage through E. coli XL 1-blue and were used for additional rounds of binding selections. After 5 rounds, we select 12 individual clones from each library and grow them in a 96-well format in 500 µl of 2YT broth supplemented with carbenicillin and M13-KO7 helper phage. Two-fold serial diluted culture supernatants were added directly in 384 well plates by coated with C3b, anti-gD, BSA and unrelated protein as designed positions. Binding affinity was measured to estimate a phage concentration giving C3b significant higher than anti-gD but not to BSA and unrelated protein. We fixed the phage concentration, screening about 200 clones from each library in the same format and selected 24-48 clones in which showed significantly to bind to C3b over anti-gD from each library, then sequence them for analysis.

Competitive Phage ELISA

For estimating the binding affinity, a modified phage ELISA was used. The 96 well microtiter plates were coat with 2 ug/ml 3Cb in 50 mM carbonate buffer (pH9.6) at 4C overnight. The plates were then block with PBS, 0.5% BSA for 1 hour at room temperature. Phage displaying CRIg variants serially diluted in PBT buffer and binding was measured to estimate a phage concentration giving 50% of the signal at saturation. Subsaturating concentration of phage was fixed and pre-incubated for 2 h with serial dilutions of C3b, then transferred the mixture to assay plates coated with C3b. After incubating 15 min, the plates were washed with PBS, 0.05% Tween 20 and incubated 30 min with horseradish peroxidase/anti-M13 antibody conjugate (1:5000 dilution in PBT buffer). The plates were washed, developed with TMB substrate, quenched with 1.0 M $H_3PO_4$, and read spectrophotometrically at 450 nm. The affinity (Ic50) was calculated as the concentration of competing C3b that resulted in half-maximal phagemid binding.

Protein Purification

A single colony of E. coli. BL21(DE3) harboring the expression plasmid was inoculated into 30 mL of LB medium supplemented with 50 µg/mL carbenicillin (LB/carb medium) and was grown overnight at 37° C. The bacteria were harvested, washed, resuspended, and inoculated into 500 mL of LB/carb medium. The culture was grown at 37° C. to mid-log phase ($A_{600}$=0.8). Protein expression was induced with 0.4 mM isopropyl 1-thio-D-galactopyranoside, and the culture was grown for 24 h at 30° C. The bacteria were pelleted by centrifugation at 4000 g for 15 min, washed twice with phosphate-buffered saline (PBS), and frozen for 8 h at −80° C. The pellet was resuspended in 50 mL of PBS, and the bacteria were lysed by passing through the Microfluidizer Processing or sonicate equipments. The CRIg variant proteins were purified with 2 ml NI-NTA agarose and gel filtration.

mutCRIg-huFc Fluid Phase Competitive Binding ELISA:

huCRIg(L)-LFH was diluted to 2 ug/mL in PBS, pH 7.4, and coated onto Maxisorp 384-well flat bottom plates (Nunc, Neptune, N.J.) by incubating overnight (16-18 hr) at 4° C. (25 ul/well). The plates were washed 3 times in Wash Buffer (PBS, pH7.4, 0.05% Tween 20), and 50 ul/well of Block Buffer (PBS, pH 7.4, 0.5% BSA) was added to each well. The plates were allowed to block for 1-3 hr; this and all subsequent incubations were performed on an orbital shaker at room temperature. During the blocking step, C3b (purified at Genentech) was diluted to 20 nM in Assay Buffer (PBS pH7.4, 0.5% BSA, 0.05% Tween-20), and the mutCRIg-huFc molecules were serially diluted in Assay Buffer, over a concentration range of 20,000-0.34 nM. The C3b and mutCRIg-huFc molecules were then mixed 1:1 and allowed to pre-incubate for 0.5-1 hr. The blocked plates were washed three times (as described above), and the C3b:mutCRIg-huFc complexes were added to the reaction plates (25 ul/well). After a 1-2 hr incubation, The ELISA plates were washed three times, (as described above) and plate-bound C3b was detected by the addition of an anti-human C3b antibody (clone 5F202, US Biological, Swampscott, Mass.; 600 ng/mL, 25 ul/well). The plates were incubated for 1-2 hr and washed as described above. HRP-conjugated anti-murine Fc IgG (Jackson ImmunoResearch, West Grove, Pa.) diluted 1:2,000 was then added (25 ul/well), and the plates were incubated for 1-2 hr. After a final wash, 25 ul/well of TMB substrate (Kirkegaard & Perry Laboratories, Gaithersburg, Md.) was added to the ELISA plates. Color development was stopped after approximately 8 min by adding 25 ul/well 1.0M phosphoric acid. Absorbance at 450 nm and 650 nm was determined using a SpectraMax 250 microtiter plate reader (Molecular Devices, Sunnyvale, Calif.).

Complement Activation Assay:

The ability of mutCRIg-Fc to inhibit complement activation was evaluated using the Wieslab™ Complement System Alternative Pathway Kit (Alpco Diagnostics, Salem, N.H.). Serially diluted mutCRIg-Fc (400 to 0.2 nM) and C1q deficient human serum (5%) (Complement Technology, Tyler, Tex.) were prepared at twice the final desired concentration, mixed 1:1, and pre-incubated for 5 min on an orbital shaker at 300 RPM prior to adding to the LPS-coated ELISA plates (100 ul/well). The remainder of the assay was following manufacturer's instructions. Briefly, the samples in the ELISA plates were incubated for 60-70 min at 37° C. and then washed three times in Wash Buffer (PBS, pH7.4, 0.05% Tween 20). 100 ul/well of the anti-C5b-9 conjugate was added to the ELISA plate. After a 30 min incubation at room temperature, the ELISA plate was washed as described above, and 100 ul of substrate was added per well, and the plates were incubated at room temperature for an additional 30 min. The color development was stopped by adding 50 ul/well of 5 mM EDTA. Absorbance at 405 nm was determined using a MultiSkan Ascent microtiter plate reader (Thermo Fisher Scientific, Milford, Mass.).

Hemolysis Inhibition Assay:

Rabbit red blood cells (Colorado Serum Company, Denver, Colo.) were washed three times with Veronal Buffer (Sigma, St. Louis, Mo.) containing 0.1% bovine skin gelatin (Sigma) (GVB), centrifuging at 1500 rpm, 4° C. for 10 minutes for each wash. After the final centrifugation step, the cells were resuspended in GVB at a final concentration of $2 \times 10^9$ cells/mL. Complement inhibitors serially diluted in GVB were added to 96-well U-bottom polypropylene plate(s) (Costar, Cambridge, Mass.) at 50 µL/well followed by 20 µL/well of rabbit red blood cells diluted 1:2 in 0.1 M $MgCl_2$/0.1 M EGTA/GVB. The in-plate complement cascade was triggered by the addition of 30 µL/well C1q-depleted serum (Complement Technology, Tyler, Tex.), pre-diluted 1:3 with GVB. The plate(s) were incubated with gentle agitation for 30 minutes at room temperature before stopping the reaction with 100 µL/well 10 mM EDTA/GVB. After centrifuging the plate(s) at 1500 rpm for 5 minutes, the supernatants were transferred to clear flat bottom, non-binding, 96-well plate(s) (Nunc, Neptune, N.J.) and the optical densities were read at 412 nm using a microplate reader (Molecular Devices, Sunnyvale, Calif.).

Alpha Screen Competitive Assay:

The potential cross-reactivity of the mutant CRIg molecules to C3 was evaluated using the AlphaScreen® Histidine (Nickel Chelate) Detection Kit (PerkinElmer, Waltham, Mass.). Serially diluted human C3 and C3b (3,000 to 0.7 nM), as well as fixed concentrations of biotinylated iC3b (30 nM), and both mutant CRIg (mutCRIg) and wild-type CRIg molecules (15-60 nM) were prepared at three times the final desired concentration, mixed 1:1:1, and pre-incubated at ambient temperature for 30 minutes on an orbital shaker at 3000 TPM. A 1:1 mixture of streptavidin donor beads and nickel chelate acceptor beads (0.1 mg/mL each) was prepared at four times the final desired concentration and added to the reaction. The reaction plate was incubated at ambient temperature for 60 minutes on an orbital shaker at 3000 rpm protected from light. The plate was analyzed on an AlphaQuest®-HTS microplate analyzer (PerkinElmer, Waltham, Mass.).

Surface Plasmon Resonance

Affinities of C3b for mutant and wild-type CRIg were determined by using surface plasmon resonance measurements on a Biacore® A100 instrument (GE healthcare). An anti-Fc capture format was employed and the $K_D$ was calculated from equilibrium binding measurements. The sensor chip was prepared using the anti-muFc capture kit (BR-1008-38) following instructions supplied by the manufacturer. Mutant or wild-type CRIg was diluted in running buffer (10 mM HEPES pH 7.4, 150 mM NaCl, 0.01% Tween-20) to 1 µg/mL and injections of 60 µL were made such that ~100 RU of fusion protein were captured on one spot of the chip surface. Sensorgrams were recorded for 10 min injections of solutions of varied C3b concentration over the CRIg spot with subtraction of signal for a reference spot containing the capture antibody but no CRIg. Data were obtained for a 2-fold dilution series of C3b ranging in concentration from 4 µM to 15.6 nM with the flow rate at 10 µL/min and at a temperature of 25° C. The surface was regenerated between binding cycles by a 30 second injection of 10 mM Gly-HCl pH 1.7. Plateau values obtained at the end of each C3b injection were used to calculate $K_D$ using the Affinity algorithm of the Biacore A100 Evaluation Software v1.1 (Safsten et al. (2006) Anal. Biochem. 353:181).

Results

Phage Library Design

We used the crystal structure of CRIg in complex with C3b to design target libraries. Five libraries were designed to cover the contact area between CRIg and C3b (FIG. 4). CRIg libraries were constructed as a fusion to the g3p minor coat protein in a monovalent phage display vector (Zhang et al., *J Biol Chem* 281(31): 22299-311 (2006)). We introduced stop codons by mutagenesis into the CRIg-coding portion of the phage plasmid at each residue to be randomized. Each construct containing a stop-codon was then used to generate the phage-display library (see material and method). A "soft randomization" strategy was used to select binders to maintain a wild-type sequence bias such that the selected positions were mutated only 50% of the time. All five libraries were obtained with an average diversity of $>10^{10}$ independent sequences per library. (FIG. 10).

Selections with CRIg Phage Library

Following four rounds of binding selection, we obtained 38 unique clones from thes five libraries. (FIG. 11). In library 1, lysine at position 15 was conserved. Aromatic residues, tyrosine and tryptophan, replaced glutamic acid at position 8. Position 14 was occupied by either the parental tryptophan or a homologous phenylalanine. In library 2, we sequenced 24 clones and all of them revealed consensus. Position 42, 46 and 47 were conserved as wild type. Asparagin, histidine and phenylalanine replaced the wild type sequence at position 43, 44 and 45. In library 3, we randomized 10 positions and the sequences exhibited complete conservation at position 54, 55, 56, 57, 58, 61, 62 and 63. Isoleucine or lysine was occupied at position 60. At position 64, glutamine was replaced by arginine or conserved. In library 4, aromatic residues dominated at position 86 and homologous basic residues, arginine and lysine, dominated at position 99. Position 85, 87 and 95 were also soft randomized, but appeared highly conserved. In library 5, two significant homologous basic residues, lysine and arginine were preferred over glutamine at position 105. Negatively charged residues, aspartic acid or acidic residues, asparagine was dominated at position 110.

We estimated the affinities of some of the mutants by competitive phage ELISA (data not shown), and we found that there were clones in library 3 which were approximately eightfold times better C3b binders than wild type CRIg.

Determination of In Vitro Binding Affinity and In Vivo Biological Potency

In order to identify critical residues for increasing the binding affinity to C3b and potency in hemolytic inhibition assay, the next approach was to design second generation of CRIg variants by incorporating dominant single mutation and keep other positions as wild type, or choosing 2-3 high-affinity clones from first generation phage-libraries which were determined by phage ELISA. In order to accurately measure the affinity and potency of our mutants, we expressed all the variants as isolated proteins. The results (FIG. 12) from hemolytic inhibition assay showed that L12 from library 1, L33 from library 3 and L41 from library 4 significantly increased the potency by 4 to 10 fold compare to wild type in a hemolytic assay. L32 from library 3 showed a 10 fold improved IC50 compared to wild type CRIg. The data also demonstrated that the binding affinity and the potency from the cell-based assays were not correlated.

Combination of Mutants

Figure 5:
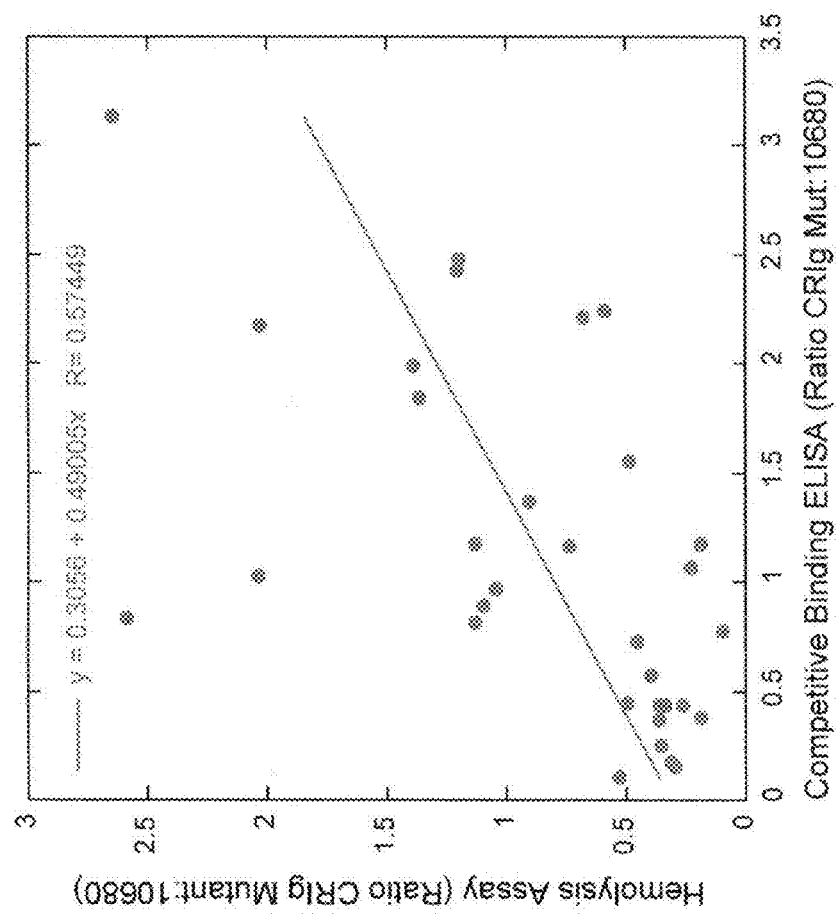
FIG. 5: Correlation between competitive ELISA and hemolytic assay.
Figure 7:
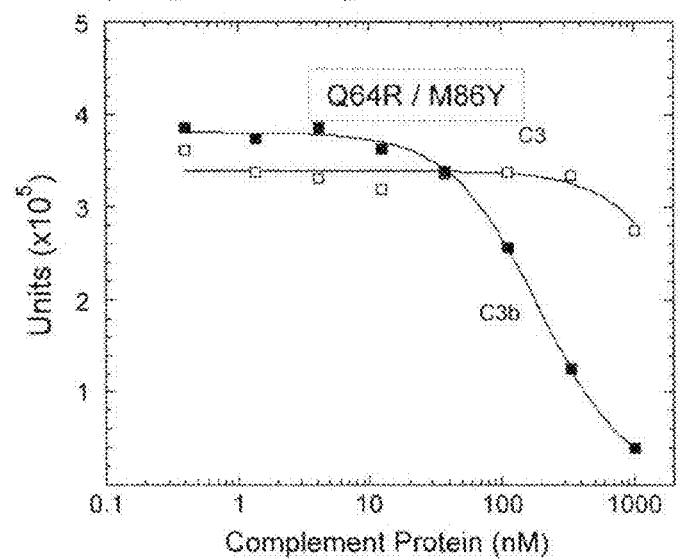
FIG. 7: Affinity-improved CRIg remains selective for C3b. Alpha Screen competitive assay was utilized on purified C3 and C3b.
Figure 8A:
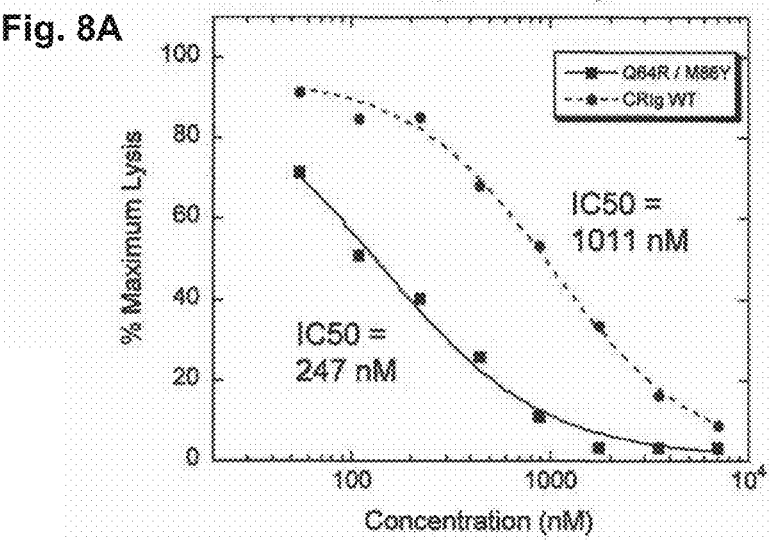
FIG. 8: Improved complement inhibitory potency of CRIg Q64R M86Y compared to wildtype CRIg. (A) Complement inhibition by wild-type CRIg and CRIg Q46R M86Y were compared using an alternative pathway-selective hemolytic assay using rabbit red blood cells and C1q-depleted human serum. (B) Complement inhibition by wild-type CRIg and CRIg Q46R M86Y were compared using an ELISA-based alternative pathway assay with microwell plate-coated LPS and C1q-depleted human serum.
Figure 8B:
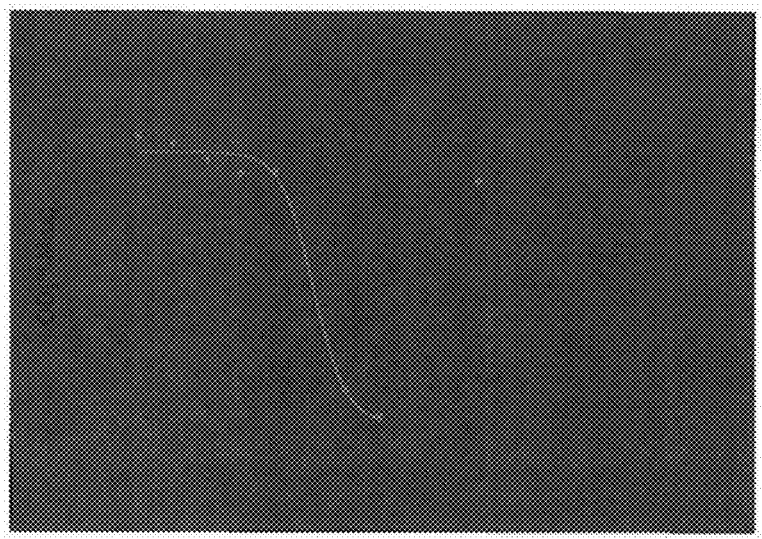
Figure 9A:
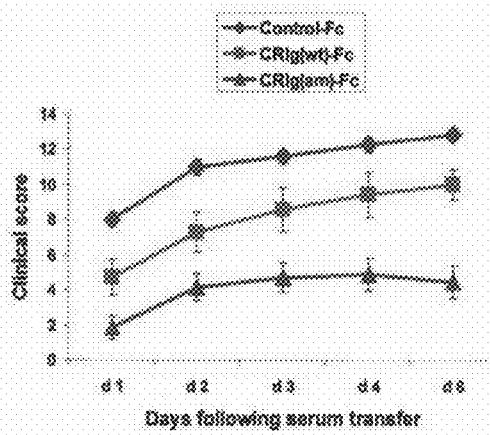
FIG. 9: CRIg Q64R M86Y shows improved efficacy in vivo over CRIg WT.
Figure 9B:
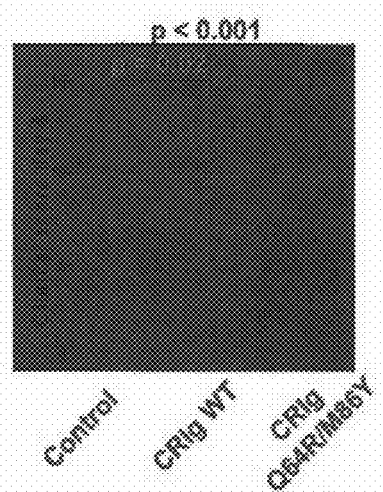
Figure 9C:
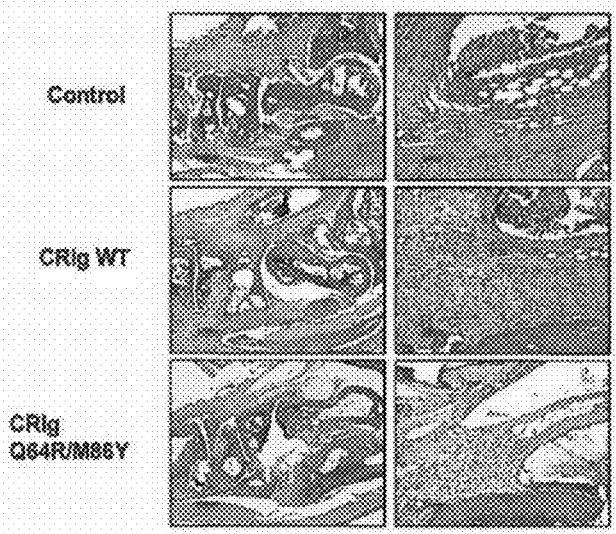
Figure 9D:
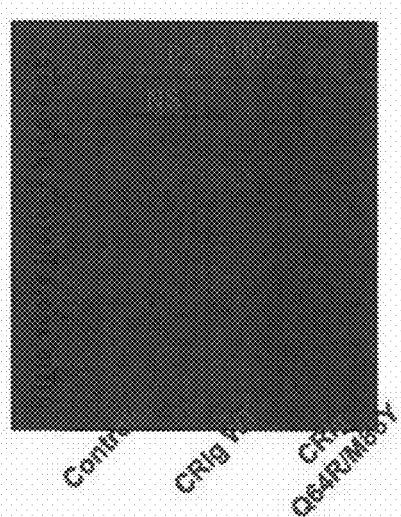

Based on the results from the second generation labraries, we designed the third generation of mutants in order to further improve the potency in the hemolytic assay and binding affinity. We chose three of the biologically most potent mutants (L12-8W, L33-Q60I/L32-Q64R and L41-M86Y) and one of the highest binding affinity mutant (L32-Q64R) as a template. Then we combined these mutants with other biological potent clones obtained in the second generation of libraries to determine an optimal set of mutations that increase potency in the hemolytic assay and binding affinity. We expressed and purified the CRIg variants for detailed analysis. The data showed (FIG. 13) that the combo mutants from L12 didn't improve inhibition potency and even displayed a lower activity compare with the parent mutant despite a 3-6 fold higher binding affinity of the WL41 and WL59 mutants. Within the mutants from L32, RL41 demonstrated a 1.8 fold better binding affinity than wild type and a 6 fold better potency in the hemolytic assay. All the mutants from L33 group showed the significant increased binding affinity; about a 27-226 fold increase compared with wild type although the potency in the hemolysis assay did not increase significantly. We also noticed that 60I-64R and 86Y was involved in most the affinity improved combo clones.

Improved Binding Affinity and Complement Inhibitory Activity of CRIg Q64R M86Y Mutant We selected mutant Q64R M86Y, which had the highest affinity in the competitive ELISA (FIG. 4 and FIG. 12) for further analysis. In order to determine the binding affinity of CRIg wt and CRIg Q64R M86Y for C3b, Biacore analysis of CRIg wt and CRIg Q64R M86Y was performed. The affinity of CRIg Q64R M86Y was improved 5 fold over wildtype CRIg (FIG. 6). Previous studies have shown that CRIg wt selectively binds to C3b but not to native C3 (Wiesman et al., Nature, 444(7116):217-20, 2006). Since mutagenesis may change this selectivity we compared the affinity of CRIg Q64R M86Y for C3b versus C3 in an alpha-screen fluid-phase competitive assay. CRIg Q64R M86Y competed with soluble C3b, but not with soluble C3, indicating that mutagenesis did not affect the selectivity of CRIg for the active component C3b (FIG. 7). This selectivity was further confirmed by analysis of these residues in the structure of CRIg Q64R M86Y in complex with C3b (data not shown).

To test whether the improved affinity and conserved selectivity for C3b translates into improved efficacy, we tested CRIg Q64R M86Y versus CRIg wt in an erythrocyte-based hemolytic assay selective for the alternative pathway of complement. CRIg Q64R M86Y showed a 4-fold improved IC50 as compared to CRIg wt (FIG. 8A). To further substantiate improved potency toward alternative pathway complement inhibiton, we compared inhibitory activity of CRIg Q64R M86Y with CRIg wt in a LPS-based assay selective for the alternative pathway of complement. Here, CRIg showed a 180-fold improvement in IC50 as compared to the wildtype recombinant protein. CRIg wt and CRIg Q64R M86Y did not affect complement activation through the classical pathway. Thus, a two amino acid substitution in the CRIg-C3b binding interface results in a molecule with improved binding affinity and superior complement inhibitory activity in two different assays with selectivity for the alternative pathway of complement.

To further determine whether increased binding affinity and potency translate into improved therapeutic efficacy, we compared the protective effect of wt and Q64R M86Y version of CRIg in a serum-transfer model of arthritis. Previous studies have shown that CRIg potently inhibits inflammation and bone destruction in collagen- and antibody-induced arthritis (Katschke et al., J. Exp Med 204(6):1319-1325 (2007)).

Here, CRIg efficacy was tested in a third preclinical model of immune complex-mediated arthritis. A spontaneous murine model of rheumatoid arthritis, K/BxN, mimics many of the clinical and histologic features of human disease with arthritis. Mice were injected with 50 microliter serum obtained from K/B×N mice on day 0. Animals were checked daily and the extent of disease was scored by visual observation. All mice were sacrificed on day 6.

Mice were injected subcutaneously with indicated amount of either isotype control or hCRIg-mIgG1 or hCRIg-RL41-mIgG1 recombinant proteins daily in 100 ul sterile saline starting on day −1.

Monitoring and Scoring:

Score for each paw.

0=No evidence of erythema and swelling

1=Erythema and mild swelling confined to the mid-foot (tarsal) or ankle

2=Erythema and mild swelling extending from the ankle to the mid-foot

3=Erythema and moderate swelling extending from the ankle to the metatarsal joints 4=Erythema and severe swelling encompass the ankle, foot and digits Mean score=sum of the 4 paw scores.

Disease stages, mild (mean score 1-3), moderate (mean score 4-8) and severe disease (mean score 9-above). The mean score reflects the number of joints involved.

On day 6, blood sample were collected by intracardiac puncture under anesthesia before sacrifice. The amount of hCRIg-Fc fusion proteins will be measured using the serum. Joints were collected for histology evaluation.

Transfer of serum from KRN mice into Balb/c recipients results in a rapid and robust immune response characterized by symmetric inflammation of the joints. Arthritis induction is mediated by anti Glucose-6-phosphate isomerase autoantibodies that form pro-inflammatory immune complexes in the joints (Kouskoff, V., Korganow, A. S., Duchatelle, V., Degott, C., Benoist, C., and Mathis, D. (1996). Organ-specific disease provoked by systemic autoimmunity. Cell 87, 811-822.) Development of arthritis is fully dependent on an intact alternative complement pathway and on Fc receptor function as shown by the lack of disease in mice deficient in alternative pathway complement components and in mice deficient in the common fc-receptor gamma chain (Ji, H., Ohmura, K., Mahmood, U., Lee, D. M., Hofluis, F. M., Boackle, S. A., Takahashi, K., Holers, V. M., Walport, M., Gerard, C., et al. (2002). Arthritis critically dependent on innate immune system players. Immunity 16, 157-168.) Due to the rapid onset and severity of disease, treatment with CRIg wt-Fc fusion protein reduced arthritis scores by only 22% (FIGS. 9A, B). Treatment with CRIg Q64R M86Y showed a reduction in arthritis scores by 66%. Histological examination showed a significant reduction in infiltration of immune cells consisting primarily of neutrophils and macrophages in CRIg Q64R M86Y treated mice versus CRIg wt or control fusion protein-treated mice (FIGS. 9C, D). Serum concentrations of CRIg wt and CRIg Q64R M86Y were similar indicating that the difference in arthritis scores was not due to a difference of halflife of the CRIg wt versus CRIg Q64R M86Y protein. Thus, we show that increased binding affinity of CRIg to its target C3b translates into a significantly improved therapeutic efficacy.

All patent and literature references cited in the present specification are hereby expressly incorporated by reference in their entirety.

While the present invention has been described with reference to what are considered to be the specific embodiments, it is to be understood that the invention is not limited to such embodiments. To the contrary, the invention is intended to cover various modifications and equivalents included within the spirit and scope of the appended claims.

What is claimed is:

1. A CRIg variant or fragment of the ECD thereof comprising an amino acid substitution at one or more amino acid positions in the amino acid sequence of SEQ ID NO:68, wherein one or more substitutions is selected from the group consisting of E8W or Y; W14F; G42D; D44H; P45F; Q60I or K; Q64R; M86Y, W, or F; Q99R or K; Q105R or K; or K110D, N or Q; and wherein the CRIg variant or fragment thereof has at least a 2-fold increased binding affinity to C3b over native sequence human CRIg of SEQ ID NO:68 or at least 2-times more potent an inhibitor of the alternative complement pathway than native sequence human CRIg of SEQ ID NO:68.

2. The variant of claim 1 which selectively binds to C3b over C3, or a fragment thereof.

3. The variant of claim 1 which has increased binding affinity to C3b over native sequence human CRIg of SEQ ID NO:68.

4. The variant of claim 3 wherein the binding affinity is increased by at least 2 fold.

5. The variant of claim 3 wherein the binding affinity is increased by at least 5 fold.

6. The variant of claim 3 wherein the binding affinity is increased by at least 10 fold.

7. The variant of claim 3 wherein the binding affinity is increased by at least 90 fold.

8. The variant of claim 1 which is a more potent inhibitor of the alternative complement pathway than native sequence human CRIg of SEQ ID NO:68.

9. The variant of claim 8 which is at least 2-times more potent than native sequence human CRIg of SEQ ID NO:68.

10. The variant of claim 8 which is at least 5-times more potent than native sequence human CRIg of SEQ ID NO:68.

11. The variant of claim 8 which is at least 10-times more potent than native sequence human CRIg of SEQ ID NO:68.

12. The variant of claim 1 comprising an amino acid substitution at one or more of amino acid positions 60, 64, 86, 99, 105 and 110 in the amino acid sequence of SEQ ID N0:68.

13. The variant of claim 1 comprising one or more substitutions selected from the group consisting of E8W, W14F, E8Y/W14F; P45F; G42D/D44H/P45F; Q60; Q64R; Q60I/Q64R; M86Y; M86W, M86F, M86W/Q99R; M86F/Q99R; K110D, K110N; Q105R/K110N; Q105R/K110Q; and Q105K/K110D.

14. The variant of claim 1 comprising one or more substitutions selected from the group consisting of Q64R/M86Y; Q60I/Q64R/E8Y; Q60I/Q64R/G42D; Q60I/Q64R/P45F; Q60I/Q64R/G42D/D44H/P45F; Q60I/Q64R/M86Y; Q60I/Q64R/Q105R; Q60I/Q64R/Q105K; Q60I/Q64R/K110N; Q60I/Q105R/K110N; M86Y/E8Y; M86Y/G42D/D44H/P45F; M86Y/P45F; M86Y/G42D/D44H/P45F; M86Y/Q99K; M86Y/Q99R; M86Y/Q105R; M86Y/Q105K; and M86Y/Q105R/K110N.

15. The variant of claim 1 comprising one or more substitutions selected from the group consisting of Q60I; Q64R; Q60I/Q64R; M86Y; Q99L; Q105K/K110D; E8W/Q105R/K110N; Q64R/M86Y; Q60I/Q64R/E8Y; Q60I/Q64R/G42D; Q60I/Q64R/P45F; Q60I/Q64R/G42D/D44H/P45F; Q60I/Q64R/M86Y; Q60I/Q64R/Q105R; Q60I/Q64R/Q105K; Q60I/Q64R/K110N; M86Y/P45F; and M86Y/Q105K.

16. The variant of claim 1 comprising a Q60I/Q64R/M86Y or Q60I/Q64R/G42D/D44H/P45F substitution.

17. A chimeric molecule comprising a variant according to claim 1.

18. The chimeric molecule of claim 17 which is an immunoadhesin.

19. The chimeric molecule of claim 18 wherein said CRIg variant is shorter than the mature full-length CRIg of SEQ ID NO:68.

20. The chimeric molecule of claim 19 comprising a CRIg extracellular domain.

21. A pharmaceutical composition comprising a CRIg variant according to claim 1, in admixture with a pharmaceutically acceptable excipient.

22. A pharmaceutical composition comprising an immunoadhesin according to claim 18, in admixture with a pharmaceutically acceptable excipient.

* * * * *

SEQUENCE LISTING

```
<160> NUMBER OF SEQ ID NOS: 68

<210> SEQ ID NO 1
<211> LENGTH: 1372
<212> TYPE: DNA
<213> ORGANISM: Homo sapiens
<220> FEATURE:
<221> NAME/KEY: CDS
<222> LOCATION: (65)..(1261)

<400> SEQUENCE: 1
ccaactgcac ctcggttcta tcgataggag gctggaagaa aggacagaag tagctctggc        60 tgtg atg ggg atc tta ctg ggc ctg cta ctc ctg ggg cac cta aca gtg       109
     Met Gly Ile Leu Leu Gly Leu Leu Leu Leu Gly His Leu Thr Val
     1               5                   10                  15 gac act tat ggc cgt ccc atc ctg gaa gtg cca gag agt gta aca gga       157
Asp Thr Tyr Gly Arg Pro Ile Leu Glu Val Pro Glu Ser Val Thr Gly
                20                  25                  30 cct tgg aaa ggg gat gtg aat ctt ccc tgc acc tat gac ccc ctg caa       205
Pro Trp Lys Gly Asp Val Asn Leu Pro Cys Thr Tyr Asp Pro Leu Gln
            35                  40                  45 ggc tac acc caa gtc ttg gtg aag tgg ctg gta caa cgt ggc tca gac       253
Gly Tyr Thr Gln Val Leu Val Lys Trp Leu Val Gln Arg Gly Ser Asp
        50                  55                  60 cct gtc acc atc ttt cta cgt gac tct tct gga gac cat atc cag cag       301
Pro Val Thr Ile Phe Leu Arg Asp Ser Ser Gly Asp His Ile Gln Gln
    65                  70                  75 gca aag tac cag ggc cgc ctg cat gtg agc cac aag gtt cca gga gat       349
Ala Lys Tyr Gln Gly Arg Leu His Val Ser His Lys Val Pro Gly Asp
80                  85                  90                  95 gta tcc ctc caa ttg agc acc ctg gag atg gat gac cgg agc cac tac       397
Val Ser Leu Gln Leu Ser Thr Leu Glu Met Asp Asp Arg Ser His Tyr
                100                 105                 110 acg tgt gaa gtc acc tgg cag act cct gat ggc aac caa gtc gtg aga       445
Thr Cys Glu Val Thr Trp Gln Thr Pro Asp Gly Asn Gln Val Val Arg
            115                 120                 125 gat aag att act gag ctc cgt gtc cag aaa ctc tct gtc tcc aag ccc       493
Asp Lys Ile Thr Glu Leu Arg Val Gln Lys Leu Ser Val Ser Lys Pro
        130                 135                 140 aca gtg aca act ggc agc ggt tat ggc ttc acg gtg ccc cag gga atg       541
Thr Val Thr Thr Gly Ser Gly Tyr Gly Phe Thr Val Pro Gln Gly Met
    145                 150                 155 agg att agc ctt caa tgc cag gct cgg ggt tct cct ccc atc agt tat       589
Arg Ile Ser Leu Gln Cys Gln Ala Arg Gly Ser Pro Pro Ile Ser Tyr
160                 165                 170                 175 att tgg tat aag caa cag act aat aac cag gaa ccc atc aaa gta gca       637
Ile Trp Tyr Lys Gln Gln Thr Asn Asn Gln Glu Pro Ile Lys Val Ala
                180                 185                 190 acc cta agt acc tta ctc ttc aag cct gcg gtg ata gcc gac tca ggc       685
Thr Leu Ser Thr Leu Leu Phe Lys Pro Ala Val Ile Ala Asp Ser Gly
            195                 200                 205
```

| | | |
|---|---|---|
| tcc tat ttc tgc act gcc aag ggc cag gtt ggc tct gag cag cac agc<br>Ser Tyr Phe Cys Thr Ala Lys Gly Gln Val Gly Ser Glu Gln His Ser<br>210 215 220 | | 733 |
| gac att gtg aag ttt gtg gtc aaa gac tcc tca aag cta ctc aag acc<br>Asp Ile Val Lys Phe Val Val Lys Asp Ser Ser Lys Leu Leu Lys Thr<br>225 230 235 | | 781 |
| aag act gag gca cct aca acc atg aca tac ccc ttg aaa gca aca tct<br>Lys Thr Glu Ala Pro Thr Thr Met Thr Tyr Pro Leu Lys Ala Thr Ser<br>240 245 250 255 | | 829 |
| aca gtg aag cag tcc tgg gac tgg acc act gac atg gat ggc tac ctt<br>Thr Val Lys Gln Ser Trp Asp Trp Thr Thr Asp Met Asp Gly Tyr Leu<br>260 265 270 | | 877 |
| gga gag acc agt gct ggg cca gga aag agc ctg cct gtc ttt gcc atc<br>Gly Glu Thr Ser Ala Gly Pro Gly Lys Ser Leu Pro Val Phe Ala Ile<br>275 280 285 | | 925 |
| atc ctc atc atc tcc ttg tgc tgt atg gtg gtt ttt acc atg gcc tat<br>Ile Leu Ile Ile Ser Leu Cys Cys Met Val Val Phe Thr Met Ala Tyr<br>290 295 300 | | 973 |
| atc atg ctc tgt cgg aag aca tcc caa caa gag cat gtc tac gaa gca<br>Ile Met Leu Cys Arg Lys Thr Ser Gln Gln Glu His Val Tyr Glu Ala<br>305 310 315 | | 1021 |
| gcc agg gca cat gcc aga gag gcc aac gac tct gga gaa acc atg agg<br>Ala Arg Ala His Ala Arg Glu Ala Asn Asp Ser Gly Glu Thr Met Arg<br>320 325 330 335 | | 1069 |
| gtg gcc atc ttc gca agt ggc tgc tcc agt gat gag cca act tcc cag<br>Val Ala Ile Phe Ala Ser Gly Cys Ser Ser Asp Glu Pro Thr Ser Gln<br>340 345 350 | | 1117 |
| aat ctg ggc aac aac tac tct gat gag ccc tgc ata gga cag gag tac<br>Asn Leu Gly Asn Asn Tyr Ser Asp Glu Pro Cys Ile Gly Gln Glu Tyr<br>355 360 365 | | 1165 |
| cag atc atc gcc cag atc aat ggc aac tac gcc cgc ctg ctg gac aca<br>Gln Ile Ile Ala Gln Ile Asn Gly Asn Tyr Ala Arg Leu Leu Asp Thr<br>370 375 380 | | 1213 |
| gtt cct ctg gat tat gag ttt ctg gcc act gag ggc aaa agt gtc tgt<br>Val Pro Leu Asp Tyr Glu Phe Leu Ala Thr Glu Gly Lys Ser Val Cys<br>385 390 395 | | 1261 |
| taaaaatgcc ccattaggcc aggatctgct gacataatct agagtcgacc tgcagaagct | | 1321 |
| tggccgccat ggcccaactt gtttattgca gcttataatg gttacaaata a | | 1372 |

<210> SEQ ID NO 2
<211> LENGTH: 399
<212> TYPE: PRT
<213> ORGANISM: Homo sapiens

<400> SEQUENCE: 2

Met Gly Ile Leu Leu Gly Leu Leu Leu Gly His Leu Thr Val Asp
1               5                   10                  15

Thr Tyr Gly Arg Pro Ile Leu Glu Val Pro Glu Ser Val Thr Gly Pro
            20                  25                  30

Trp Lys Gly Asp Val Asn Leu Pro Cys Thr Tyr Asp Pro Leu Gln Gly
        35                  40                  45

Tyr Thr Gln Val Leu Val Lys Trp Leu Val Arg Gly Ser Asp Pro
    50                  55                  60

Val Thr Ile Phe Leu Arg Asp Ser Ser Gly Asp His Ile Gln Gln Ala
65                  70                  75                  80

Lys Tyr Gln Gly Arg Leu His Val Ser His Lys Val Pro Gly Asp Val
                85                  90                  95

Ser Leu Gln Leu Ser Thr Leu Glu Met Asp Asp Arg Ser His Tyr Thr

-continued

```
                100                 105                 110
        Cys Glu Val Thr Trp Gln Thr Pro Asp Gly Asn Gln Val Arg Asp
            115                 120                 125
        Lys Ile Thr Glu Leu Arg Val Gln Lys Leu Ser Val Ser Lys Pro Thr
        130                 135                 140
        Val Thr Thr Gly Ser Gly Tyr Gly Phe Thr Val Pro Gln Gly Met Arg
        145                 150                 155                 160
        Ile Ser Leu Gln Cys Gln Ala Arg Gly Ser Pro Pro Ile Ser Tyr Ile
                        165                 170                 175
        Trp Tyr Lys Gln Gln Thr Asn Asn Gln Glu Pro Ile Lys Val Ala Thr
                    180                 185                 190
        Leu Ser Thr Leu Leu Phe Lys Pro Ala Val Ile Ala Asp Ser Gly Ser
                195                 200                 205
        Tyr Phe Cys Thr Ala Lys Gly Gln Val Gly Ser Glu Gln His Ser Asp
            210                 215                 220
        Ile Val Lys Phe Val Val Lys Asp Ser Ser Lys Leu Leu Lys Thr Lys
        225                 230                 235                 240
        Thr Glu Ala Pro Thr Thr Met Thr Tyr Pro Leu Lys Ala Thr Ser Thr
                        245                 250                 255
        Val Lys Gln Ser Trp Asp Trp Thr Thr Asp Met Asp Gly Tyr Leu Gly
                    260                 265                 270
        Glu Thr Ser Ala Gly Pro Gly Lys Ser Leu Pro Val Phe Ala Ile Ile
                275                 280                 285
        Leu Ile Ile Ser Leu Cys Cys Met Val Val Phe Thr Met Ala Tyr Ile
            290                 295                 300
        Met Leu Cys Arg Lys Thr Ser Gln Gln Glu His Val Tyr Glu Ala Ala
        305                 310                 315                 320
        Arg Ala His Ala Arg Glu Ala Asn Asp Ser Gly Glu Thr Met Arg Val
                        325                 330                 335
        Ala Ile Phe Ala Ser Gly Cys Ser Ser Asp Glu Pro Thr Ser Gln Asn
                    340                 345                 350
        Leu Gly Asn Asn Tyr Ser Asp Glu Pro Cys Ile Gly Gln Glu Tyr Gln
                355                 360                 365
        Ile Ile Ala Gln Ile Asn Gly Asn Tyr Ala Arg Leu Leu Asp Thr Val
            370                 375                 380
        Pro Leu Asp Tyr Glu Phe Leu Ala Thr Glu Gly Lys Ser Val Cys
        385                 390                 395

<210> SEQ ID NO 3
<211> LENGTH: 1090
<212> TYPE: DNA
<213> ORGANISM: Homo sapiens
<220> FEATURE:
<221> NAME/KEY: CDS
<222> LOCATION: (67)..(981)

<400> SEQUENCE: 3
gtccaactgc acctcggttc tatcgatagg aggctggaag aaaggacaga agtagctctg      60 gctgtg atg ggg atc tta ctg ggc ctg cta ctc ctg ggg cac cta aca        108
       Met Gly Ile Leu Leu Gly Leu Leu Leu Leu Gly His Leu Thr
         1               5                  10 gtg gac act tat ggc cgt ccc atc ctg gaa gtg cca gag agt gta aca       156
Val Asp Thr Tyr Gly Arg Pro Ile Leu Glu Val Pro Glu Ser Val Thr
 15              20                  25                  30 gga cct tgg aaa ggg gat gtg aat ctt ccc tgc acc tat gac ccc ctg       204
Gly Pro Trp Lys Gly Asp Val Asn Leu Pro Cys Thr Tyr Asp Pro Leu
```

```
                  35                  40                  45
caa ggc tac acc caa gtc ttg gtg aag tgg ctg gta caa cgt ggc tca      252
Gln Gly Tyr Thr Gln Val Leu Val Lys Trp Leu Val Gln Arg Gly Ser
         50                  55                  60 gac cct gtc acc atc ttt cta cgt gac tct tct gga gac cat atc cag      300
Asp Pro Val Thr Ile Phe Leu Arg Asp Ser Ser Gly Asp His Ile Gln
     65                  70                  75 cag gca aag tac cag ggc cgc ctg cat gtg agc cac aag gtt cca gga      348
Gln Ala Lys Tyr Gln Gly Arg Leu His Val Ser His Lys Val Pro Gly
 80                  85                  90 gat gta tcc ctc caa ttg agc acc ctg gag atg gat gac cgg agc cac      396
Asp Val Ser Leu Gln Leu Ser Thr Leu Glu Met Asp Asp Arg Ser His
95                 100                 105                 110 tac acg tgt gaa gtc acc tgg cag act cct gat ggc aac caa gtc gtg      444
Tyr Thr Cys Glu Val Thr Trp Gln Thr Pro Asp Gly Asn Gln Val Val
                115                 120                 125 aga gat aag att act gag ctc cgt gtc cag aaa cac tcc tca aag cta      492
Arg Asp Lys Ile Thr Glu Leu Arg Val Gln Lys His Ser Ser Lys Leu
            130                 135                 140 ctc aag acc aag act gag gca cct aca acc atg aca tac ccc ttg aaa      540
Leu Lys Thr Lys Thr Glu Ala Pro Thr Thr Met Thr Tyr Pro Leu Lys
        145                 150                 155 gca aca tct aca gtg aag cag tcc tgg gac tgg acc act gac atg gat      588
Ala Thr Ser Thr Val Lys Gln Ser Trp Asp Trp Thr Thr Asp Met Asp
    160                 165                 170 ggc tac ctt gga gag acc agt gct ggg cca gga aag agc ctg cct gtc      636
Gly Tyr Leu Gly Glu Thr Ser Ala Gly Pro Gly Lys Ser Leu Pro Val
175                 180                 185                 190 ttt gcc atc atc ctc atc atc tcc ttg tgc tgt atg gtg gtt ttt acc      684
Phe Ala Ile Ile Leu Ile Ile Ser Leu Cys Cys Met Val Val Phe Thr
                195                 200                 205 atg gcc tat atc atg ctc tgt cgg aag aca tcc caa caa gag cat gtc      732
Met Ala Tyr Ile Met Leu Cys Arg Lys Thr Ser Gln Gln Glu His Val
            210                 215                 220 tac gaa gca gcc agg gca cat gcc aga gag gcc aac gac tct gga gaa      780
Tyr Glu Ala Ala Arg Ala His Ala Arg Glu Ala Asn Asp Ser Gly Glu
        225                 230                 235 acc atg agg gtg gcc atc ttc gca agt ggc tgc tcc agt gat gag cca      828
Thr Met Arg Val Ala Ile Phe Ala Ser Gly Cys Ser Ser Asp Glu Pro
    240                 245                 250 act tcc cag aat ctg ggc aac aac tac tct gat gag ccc tgc ata gga      876
Thr Ser Gln Asn Leu Gly Asn Asn Tyr Ser Asp Glu Pro Cys Ile Gly
255                 260                 265                 270 cag gag tac cag atc atc gcc cag atc aat ggc aac tac gcc cgc ctg      924
Gln Glu Tyr Gln Ile Ile Ala Gln Ile Asn Gly Asn Tyr Ala Arg Leu
                275                 280                 285 ctg gac aca gtt cct ctg gat tat gag ttt ctg gcc act gag ggc aaa      972
Leu Asp Thr Val Pro Leu Asp Tyr Glu Phe Leu Ala Thr Glu Gly Lys
            290                 295                 300 agt gtc tgt taaaaatgcc ccattaggcc aggatctgct gacataatct             1021
Ser Val Cys
        305 agagtcgacc tgcagaagct tggccgccat ggcccaactt gtttattgca gcttataatg    1081 gttacaata                                                            1090

<210> SEQ ID NO 4
<211> LENGTH: 305
<212> TYPE: PRT
<213> ORGANISM: Homo sapiens
```

<400> SEQUENCE: 4

```
Met Gly Ile Leu Leu Gly Leu Leu Leu Gly His Leu Thr Val Asp
1               5                   10                  15

Thr Tyr Gly Arg Pro Ile Leu Glu Val Pro Glu Ser Val Thr Gly Pro
            20                  25                  30

Trp Lys Gly Asp Val Asn Leu Pro Cys Thr Tyr Asp Pro Leu Gln Gly
        35                  40                  45

Tyr Thr Gln Val Leu Val Lys Trp Leu Val Gln Arg Gly Ser Asp Pro
    50                  55                  60

Val Thr Ile Phe Leu Arg Asp Ser Ser Gly Asp His Ile Gln Gln Ala
65                  70                  75                  80

Lys Tyr Gln Gly Arg Leu His Val Ser His Lys Val Pro Gly Asp Val
                85                  90                  95

Ser Leu Gln Leu Ser Thr Leu Glu Met Asp Asp Arg Ser His Tyr Thr
            100                 105                 110

Cys Glu Val Thr Trp Gln Thr Pro Asp Gly Asn Gln Val Val Arg Asp
        115                 120                 125

Lys Ile Thr Glu Leu Arg Val Gln Lys His Ser Ser Lys Leu Leu Lys
    130                 135                 140

Thr Lys Thr Glu Ala Pro Thr Thr Met Thr Tyr Pro Leu Lys Ala Thr
145                 150                 155                 160

Ser Thr Val Lys Gln Ser Trp Asp Trp Thr Thr Asp Met Asp Gly Tyr
                165                 170                 175

Leu Gly Glu Thr Ser Ala Gly Pro Gly Lys Ser Leu Pro Val Phe Ala
            180                 185                 190

Ile Ile Leu Ile Ile Ser Leu Cys Cys Met Val Val Phe Thr Met Ala
        195                 200                 205

Tyr Ile Met Leu Cys Arg Lys Thr Ser Gln Gln Glu His Val Tyr Glu
    210                 215                 220

Ala Ala Arg Ala His Ala Arg Glu Ala Asn Asp Ser Gly Glu Thr Met
225                 230                 235                 240

Arg Val Ala Ile Phe Ala Ser Gly Cys Ser Ser Asp Glu Pro Thr Ser
                245                 250                 255

Gln Asn Leu Gly Asn Asn Tyr Ser Asp Glu Pro Cys Ile Gly Gln Glu
            260                 265                 270

Tyr Gln Ile Ile Ala Gln Ile Asn Gly Asn Tyr Ala Arg Leu Leu Asp
        275                 280                 285

Thr Val Pro Leu Asp Tyr Glu Phe Leu Ala Thr Glu Gly Lys Ser Val
    290                 295                 300

Cys
305
```

<210> SEQ ID NO 5
<211> LENGTH: 1590
<212> TYPE: DNA
<213> ORGANISM: Unknown
<220> FEATURE:
<223> OTHER INFORMATION: Mus species
<220> FEATURE:
<221> NAME/KEY: CDS
<222> LOCATION: (134)..(973)

<400> SEQUENCE: 5

```
gtccaactgc acctcggttc tatcgattcg aattcggcca cactggccgg atcctctaga      60
gatccctcga cctcgaccca cgcgtccgag cagcaagagg atggaaggat gaatagaagt     120
```

-continued

| | |
|---|---|
| agcttcaaat agg atg gag atc tca tca ggc ttg ctg ttc ctg ggc cac<br>              Met Glu Ile Ser Ser Gly Leu Leu Phe Leu Gly His<br>               1                5                    10 | 169 |
| cta ata gtg ctc acc tat ggc cac ccc acc cta aaa aca cct gag agt<br>Leu Ile Val Leu Thr Tyr Gly His Pro Thr Leu Lys Thr Pro Glu Ser<br>        15                   20                   25 | 217 |
| gtg aca ggg acc tgg aaa gga gat gtg aag att cag tgc atc tat gat<br>Val Thr Gly Thr Trp Lys Gly Asp Val Lys Ile Gln Cys Ile Tyr Asp<br> 30                      35                    40 | 265 |
| ccc ctg aga ggc tac agg caa gtt ttg gtg aaa tgg ctg gta aga cac<br>Pro Leu Arg Gly Tyr Arg Gln Val Leu Val Lys Trp Leu Val Arg His<br>45                  50                   55                   60 | 313 |
| ggc tct gac tcc gtc acc atc ttc cta cgt gac tcc act gga gac cat<br>Gly Ser Asp Ser Val Thr Ile Phe Leu Arg Asp Ser Thr Gly Asp His<br>              65                   70                   75 | 361 |
| atc cag cag gca aag tac aga ggc cgc ctg aaa gtg agc cac aaa gtt<br>Ile Gln Gln Ala Lys Tyr Arg Gly Arg Leu Lys Val Ser His Lys Val<br>        80                   85                   90 | 409 |
| cca gga gat gtg tcc ctc caa ata aat acc ctg cag atg gat gac agg<br>Pro Gly Asp Val Ser Leu Gln Ile Asn Thr Leu Gln Met Asp Asp Arg<br>95                   100                    105 | 457 |
| aat cac tat aca tgt gag gtc acc tgg cag act cct gat gga aac caa<br>Asn His Tyr Thr Cys Glu Val Thr Trp Gln Thr Pro Asp Gly Asn Gln<br>        110                 115                120 | 505 |
| gta ata aga gat aag atc att gag ctc cgt gtt cgg aaa tat aat cca<br>Val Ile Arg Asp Lys Ile Ile Glu Leu Arg Val Arg Lys Tyr Asn Pro<br>125                 130                135                140 | 553 |
| cct aga atc aat act gaa gca cct aca acc ctg cac tcc tct ttg gaa<br>Pro Arg Ile Asn Thr Glu Ala Pro Thr Thr Leu His Ser Ser Leu Glu<br>             145                150                155 | 601 |
| gca aca act ata atg agt tca acc tct gac ttg acc act aat ggg act<br>Ala Thr Thr Ile Met Ser Ser Thr Ser Asp Leu Thr Thr Asn Gly Thr<br>                160                165                170 | 649 |
| gga aaa ctt gag gag acc att gct ggt tca ggg agg aac ctg cca atc<br>Gly Lys Leu Glu Glu Thr Ile Ala Gly Ser Gly Arg Asn Leu Pro Ile<br>175                 180                185 | 697 |
| ttt gcc ata atc ttc atc atc tcc ctt tgc tgc ata gta gct gtc acc<br>Phe Ala Ile Ile Phe Ile Ile Ser Leu Cys Cys Ile Val Ala Val Thr<br>     190                    195                200 | 745 |
| ata cct tat atc ttg ttc cgc tgc agg aca ttc caa caa gag tat gtc<br>Ile Pro Tyr Ile Leu Phe Arg Cys Arg Thr Phe Gln Gln Glu Tyr Val<br>205               210                215                220 | 793 |
| tat gga gtg agc agg gtg ttt gcc agg aag aca agc aac tct gaa gaa<br>Tyr Gly Val Ser Arg Val Phe Ala Arg Lys Thr Ser Asn Ser Glu Glu<br>             225                230                235 | 841 |
| acc aca agg gtg act acc atc gca act gat gaa cca gat tcc cag gct<br>Thr Thr Arg Val Thr Thr Ile Ala Thr Asp Glu Pro Asp Ser Gln Ala<br>240                 245                250 | 889 |
| ctg att agt gac tac tct gat gat cct tgc ctc agc cag gag tac caa<br>Leu Ile Ser Asp Tyr Ser Asp Asp Pro Cys Leu Ser Gln Glu Tyr Gln<br>        255               260                265 | 937 |
| ata acc atc aga tca aca atg tct att cct gcc tgc tgaacacagt<br>Ile Thr Ile Arg Ser Thr Met Ser Ile Pro Ala Cys<br>270                 275                280 | 983 |
| ttccagaaac taagaagttc ttgctactga agaaaataac atctgctaaa atgcccctac | 1043 |
| taagtcaagg tctactggcg taattacctg ttacttattt actacttgcc ttcaacatag | 1103 |
| ctttctccct ggcttccttt cttcttagac aacctaaagt atctatctag tctgccaatt | 1163 |

```
ctggggccat tgagaaatcc tgggtttggc taagaatata ctacatgcac ctcaagaaat   1223
ctagcttctg ggcttcaccc agaacaattt tcttcctagg gccttcacaa ctcttctcca   1283
aacagcagag aaattccata gcagtagagg ttctttatca tgcctccaga cagcgtgagt   1343
ctcagtccta caaactcaga caagcacatg ggtctaggat tactcctctt tctctagggc   1403
cagatgactt ttaattgata ttactattgc tacattatga atctaatgca catgtattct   1463
tttgttgtta ataaatgttt aatcatgaca tcaaaaaaaa aaaaaaaaag ggcggccgcg   1523
actctagagt cgacctgcag tagggataac agggtaataa gcttggccgc catggcccaa   1583
cttgttt                                                             1590
```

<210> SEQ ID NO 6
<211> LENGTH: 280
<212> TYPE: PRT
<213> ORGANISM: Unknown
<220> FEATURE:
<223> OTHER INFORMATION: Mus species

<400> SEQUENCE: 6

```
Met Glu Ile Ser Ser Gly Leu Leu Phe Leu Gly His Leu Ile Val Leu
1               5                   10                  15

Thr Tyr Gly His Pro Thr Leu Lys Thr Pro Glu Ser Val Thr Gly Thr
            20                  25                  30

Trp Lys Gly Asp Val Lys Ile Gln Cys Ile Tyr Asp Pro Leu Arg Gly
        35                  40                  45

Tyr Arg Gln Val Leu Val Lys Trp Leu Val Arg His Gly Ser Asp Ser
    50                  55                  60

Val Thr Ile Phe Leu Arg Asp Ser Thr Gly Asp His Ile Gln Gln Ala
65                  70                  75                  80

Lys Tyr Arg Gly Arg Leu Lys Val Ser His Lys Val Pro Gly Asp Val
                85                  90                  95

Ser Leu Gln Ile Asn Thr Leu Gln Met Asp Asp Arg Asn His Tyr Thr
            100                 105                 110

Cys Glu Val Thr Trp Gln Thr Pro Asp Gly Asn Gln Val Ile Arg Asp
        115                 120                 125

Lys Ile Ile Glu Leu Arg Val Arg Lys Tyr Asn Pro Pro Arg Ile Asn
    130                 135                 140

Thr Glu Ala Pro Thr Thr Leu His Ser Ser Leu Glu Ala Thr Thr Ile
145                 150                 155                 160

Met Ser Ser Thr Ser Asp Leu Thr Thr Asn Gly Thr Gly Lys Leu Glu
                165                 170                 175

Glu Thr Ile Ala Gly Ser Gly Arg Asn Leu Pro Ile Phe Ala Ile Ile
            180                 185                 190

Phe Ile Ile Ser Leu Cys Cys Ile Val Ala Val Thr Ile Pro Tyr Ile
        195                 200                 205

Leu Phe Arg Cys Arg Thr Phe Gln Gln Glu Tyr Val Tyr Gly Val Ser
    210                 215                 220

Arg Val Phe Ala Arg Lys Thr Ser Asn Ser Glu Glu Thr Thr Arg Val
225                 230                 235                 240

Thr Thr Ile Ala Thr Asp Glu Pro Asp Ser Gln Ala Leu Ile Ser Asp
                245                 250                 255

Tyr Ser Asp Asp Pro Cys Leu Ser Gln Glu Tyr Gln Ile Thr Ile Arg
            260                 265                 270

Ser Thr Met Ser Ile Pro Ala Cys
        275                 280
```

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(18)
<223> OTHER INFORMATION: a, c, g or t
<220> FEATURE:
<223> OTHER INFORMATION: see specification as filed for detailed
      description of substitutions and preferred embodiments

<400> SEQUENCE: 7
atcctggaag tgcaannn                                                18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(18)
<223> OTHER INFORMATION: a, c, g or t
<220> FEATURE:
<223> OTHER INFORMATION: see specification as filed for detailed
      description of substitutions and preferred embodiments

<400> SEQUENCE: 8
agtgtaacag gacctnnn                                                18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, g or t
<220> FEATURE:
<223> OTHER INFORMATION: see specification as filed for detailed
      description of substitutions and preferred embodiments

<400> SEQUENCE: 9
nnnggggatg tgaatctt                                                18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(18)
<223> OTHER INFORMATION: a, c, g or t
<220> FEATURE:
<223> OTHER INFORMATION: see specification as filed for detailed
      description of substitutions and preferred embodiments

<400> SEQUENCE: 10
aagtggctgg tacaannn                                                    18

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, g or t
<220> FEATURE:
<221> NAME/KEY: modified_base
<222> LOCATION: (7)..(18)
<223> OTHER INFORMATION: a, c, g or t
<220> FEATURE:
<223> OTHER INFORMATION: see specification as filed for detailed
      description of substitutions and preferred embodiments

<400> SEQUENCE: 11
nnntcannnn nnnnnnnnat cttt                                             24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, g or t
<220> FEATURE:
<221> NAME/KEY: modified_base
<222> LOCATION: (7)..(9)
<223> OTHER INFORMATION: a, c, g or t
<220> FEATURE:
<223> OTHER INFORMATION: see specification as filed for detailed
      description of substitutions and preferred embodiments

<400> SEQUENCE: 12
nnncgtnnnt cttctggaga ccat                                             24

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tttctacgtg actct                                                       15

<210> SEQ ID NO 14
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(27)
<223> OTHER INFORMATION: a, c, g or t
<220> FEATURE:
<221> NAME/KEY: modified_base
<222> LOCATION: (31)..(33)
<223> OTHER INFORMATION: a, c, g or t -continued

```
<220> FEATURE:
<223> OTHER INFORMATION: see specification as filed for detailed
      description of substitutions and preferred embodiments

<400> SEQUENCE: 14
nnnnnnnnnn nnnnnnnnnn nnnnnnntac nnnggccgcc tgcatgtvg                 49

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
caattgagca ccctg                                                      15

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(9)
<223> OTHER INFORMATION: a, c, g or t
<220> FEATURE:
<221> NAME/KEY: modified_base
<222> LOCATION: (13)..(15)
<223> OTHER INFORMATION: a, c, g or t
<220> FEATURE:
<221> NAME/KEY: modified_base
<222> LOCATION: (31)..(33)
<223> OTHER INFORMATION: a, c, g or t
<220> FEATURE:
<223> OTHER INFORMATION: see specification as filed for detailed
      description of substitutions and preferred embodiments

<400> SEQUENCE: 16
nnnnnnnnng acnnnagcca ctacacgtgt nnn                                  33

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(12)
<223> OTHER INFORMATION: a, c, g or t
<220> FEATURE:
<223> OTHER INFORMATION: see specification as filed for detailed
      description of substitutions and preferred embodiments

<400> SEQUENCE: 17
gtcacctggn nn                                                         12

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
```
actcctgatg gcaac                                                          15

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(18)
<223> OTHER INFORMATION: a, c, g or t
<220> FEATURE:
<223> OTHER INFORMATION: see specification as filed for detailed
      description of substitutions and preferred embodiments

<400> SEQUENCE: 19
actcctgatg gcaacnnn                                                       18

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(15)
<223> OTHER INFORMATION: a, c, g or t
<220> FEATURE:
<223> OTHER INFORMATION: see specification as filed for detailed
      description of substitutions and preferred embodiments

<400> SEQUENCE: 20
gtcnnnnnnn nnnnnattac tgagctccgt                                          30

<210> SEQ ID NO 21
<211> LENGTH: 10
<212> TYPE: PRT
<213> ORGANISM: Unknown
<220> FEATURE:
<223> OTHER INFORMATION: Description of Unknown: Unknown wild-type
      peptide

<400> SEQUENCE: 21

Pro Glu Ser Val Thr Gly Pro Trp Lys Gly
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Pro Tyr Ser Val Thr Gly Pro Trp Lys Gly
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 23

Pro Trp Ser Val Thr Gly Pro Phe Lys Gly
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Pro Tyr Ser Val Thr Gly Pro Phe Lys Gly
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: VARIANT
<222> LOCATION: (8)..(8)
<223> OTHER INFORMATION: Trp or Phe

<400> SEQUENCE: 25

Pro Tyr Ser Val Thr Gly Pro Xaa Lys Gly
1               5                   10

<210> SEQ ID NO 26
<211> LENGTH: 14
<212> TYPE: PRT
<213> ORGANISM: Unknown
<220> FEATURE:
<223> OTHER INFORMATION: Description of Unknown: Unknown wild-type
      peptide

<400> SEQUENCE: 26

Gln Arg Gly Ser Asp Pro Val Thr Ile Phe Leu Arg Asp Ser
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Arg Asp Ser His Phe Val Thr Ile Phe Leu Arg Asp Ser
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 28

Gln Arg Asp Ser His Phe Val Thr Ile Phe Leu Arg Asp Ser
1               5                   10
```

```
<210> SEQ ID NO 29
<211> LENGTH: 13
<212> TYPE: PRT
<213> ORGANISM: Unknown
<220> FEATURE:
<223> OTHER INFORMATION: Description of Unknown: Unknown wild-type
      peptide

<400> SEQUENCE: 29

Ser Ser Gly Asp His Ile Gln Gln Ala Lys Tyr Gln Gly
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Ser Gly Asp His Ile Gln Ile Ala Lys Tyr Arg Gly
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Ser Gly Asp His Ile Gln Lys Ala Lys Tyr Gln Gly
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Ser Gly Asp His Ile Gln Ile Ala Lys Tyr Gln Gly
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      Consensus sequence
<220> FEATURE:
<221> NAME/KEY: VARIANT
<222> LOCATION: (12)..(12)
<223> OTHER INFORMATION: Arg or Gln

<400> SEQUENCE: 33

Ser Ser Gly Asp His Ile Gln Ile Ala Lys Tyr Xaa Gly
1               5                   10

<210> SEQ ID NO 34
<211> LENGTH: 17
<212> TYPE: PRT
```

<213> ORGANISM: Unknown
<220> FEATURE:
<223> OTHER INFORMATION: Description of Unknown: Unknown wild-type
      peptide

<400> SEQUENCE: 34

Leu Glu Met Asp Asp Arg Ser His Tyr Thr Cys Glu Val Thr Trp Gln
1               5                   10                  15

Thr

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Glu Cys Asp Asp Gln Ser His Tyr Thr Cys Glu Val Thr Trp Tyr
1               5                   10                  15

Thr

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Glu Cys Asp Asp Arg Ser His Tyr Thr Cys Glu Val Thr Trp Arg
1               5                   10                  15

Thr

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Glu Tyr Asp Asp Arg Ser His Tyr Thr Cys Glu Val Thr Trp Lys
1               5                   10                  15

Thr

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Glu Tyr Asp Asp Arg Ser His Tyr Thr Cys Glu Val Thr Trp Lys
1               5                   10                  15

Thr

<210> SEQ ID NO 39
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Glu Tyr Asp Asp Arg Ser His Tyr Thr Cys Glu Val Thr Trp Arg
1               5                   10                  15

Thr

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Glu Tyr Asp Asp Arg Ser His Tyr Thr Cys Glu Val Thr Trp Leu
1               5                   10                  15

Thr

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Glu Tyr Asp Asp Arg Ser His Tyr Thr Cys Glu Val Thr Trp Gln
1               5                   10                  15

Thr

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Glu Tyr Asp Asp Lys Ser His Tyr Thr Cys Glu Val Thr Trp Gln
1               5                   10                  15

Thr

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Glu Trp Asp Asp Arg Ser His Tyr Thr Cys Glu Val Thr Trp Phe
1               5                   10                  15

Thr

<210> SEQ ID NO 44
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Glu Trp Asp Asp Arg Ser His Tyr Thr Cys Glu Val Thr Trp Tyr
1               5                   10                  15
Thr

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Leu Glu Trp Asp Asp Arg Ser His Tyr Thr Cys Glu Val Thr Trp Lys
1               5                   10                  15
Thr

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Glu Trp Asp Asp Arg Ser His Tyr Thr Cys Glu Val Thr Trp Arg
1               5                   10                  15
Thr

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Glu Trp Asp Asp Arg Ser His Tyr Thr Cys Glu Val Thr Trp Gln
1               5                   10                  15
Thr

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Glu Phe Asp Asp Arg Ser His Tyr Thr Cys Glu Val Thr Trp Lys
1               5                   10                  15
Thr
```

```
<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Glu Phe Asp Asp Arg Ser His Tyr Thr Cys Glu Val Thr Trp Arg
1               5                   10                  15

Thr

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: VARIANT
<222> LOCATION: (3)..(3)
<223> OTHER INFORMATION: Tyr, Trp or Phe
<220> FEATURE:
<221> NAME/KEY: VARIANT
<222> LOCATION: (16)..(16)
<223> OTHER INFORMATION: Lys or Arg

<400> SEQUENCE: 50

Leu Glu Xaa Asp Asp Arg Ser His Tyr Thr Cys Glu Val Thr Trp Xaa
1               5                   10                  15

Thr

<210> SEQ ID NO 51
<211> LENGTH: 8
<212> TYPE: PRT
<213> ORGANISM: Unknown
<220> FEATURE:
<223> OTHER INFORMATION: Description of Unknown: Unknown wild-type
      peptide

<400> SEQUENCE: 51

Asn Gln Val Val Arg Asp Lys Ile
1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asn Arg Val Val Arg Asp Asn Ile
1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asn Arg Val Val Arg Asp Asp Ile
```

```
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asn Arg Val Val Arg Asp Gln Ile
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asn Arg Val Ile Arg Asp Gln Ile
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asn Arg Val Ile Arg Asp His Ile
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asn Lys Val Ile Arg Asp Gln Ile
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asn Lys Val Ile Ala Asp Asn Ile
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                       peptide

<400> SEQUENCE: 59

Asn Lys Val Ile Ser Asp Asn Ile
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asn Gln Val Ile Arg Ser Asp Ile
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asn Lys Val Thr Arg Asp Asn Ile
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asn Lys Val Val Arg Asp Gln Ile
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asn Lys Val Val Arg Asp Asn Ile
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asn Lys Val Val Arg Asp Asp Ile
1               5

<210> SEQ ID NO 65
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asn Lys Val Val Arg Ser Asp Ile
1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asn Lys Val Val Ser Asp Asp Ile
1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: VARIANT
<222> LOCATION: (2)..(2)
<223> OTHER INFORMATION: Lys or Arg
<220> FEATURE:
<221> NAME/KEY: VARIANT
<222> LOCATION: (4)..(4)
<223> OTHER INFORMATION: Val or Ile
<220> FEATURE:
<221> NAME/KEY: VARIANT
<222> LOCATION: (7)..(7)
<223> OTHER INFORMATION: Gln, Asp or Asn

<400> SEQUENCE: 67

Asn Xaa Val Xaa Arg Asp Xaa Ile
1               5

<210> SEQ ID NO 68
<211> LENGTH: 286
<212> TYPE: PRT
<213> ORGANISM: Homo sapiens

<400> SEQUENCE: 68

Arg Pro Ile Leu Glu Val Pro Glu Ser Val Thr Gly Pro Trp Lys Gly
1               5                   10                  15

Asp Val Asn Leu Pro Cys Thr Tyr Asp Pro Leu Gln Gly Tyr Thr Gln
                20                  25                  30

Val Leu Val Lys Trp Leu Val Gln Arg Gly Ser Asp Pro Val Thr Ile
            35                  40                  45

Phe Leu Arg Asp Ser Ser Gly Asp His Ile Gln Gln Ala Lys Tyr Gln
        50                  55                  60

Gly Arg Leu His Val Ser His Lys Val Pro Gly Asp Val Ser Leu Gln
65                  70                  75                  80

Leu Ser Thr Leu Glu Met Asp Asp Arg Ser His Tyr Thr Cys Glu Val
                85                  90                  95

Thr Trp Gln Thr Pro Asp Gly Asn Gln Val Val Arg Asp Lys Ile Thr
```

-continued

```
              100                 105                 110
Glu Leu Arg Val Gln Lys His Ser Ser Lys Leu Leu Lys Thr Lys Thr
            115                 120                 125

Glu Ala Pro Thr Thr Met Thr Tyr Pro Leu Lys Ala Thr Ser Thr Val
            130                 135                 140

Lys Gln Ser Trp Asp Trp Thr Thr Asp Met Asp Gly Tyr Leu Gly Glu
145                 150                 155                 160

Thr Ser Ala Gly Pro Gly Lys Ser Leu Pro Val Phe Ala Ile Ile Leu
                165                 170                 175

Ile Ile Ser Leu Cys Cys Met Val Val Phe Thr Met Ala Tyr Ile Met
            180                 185                 190

Leu Cys Arg Lys Thr Ser Gln Gln Glu His Val Tyr Glu Ala Ala Arg
        195                 200                 205

Ala His Ala Arg Glu Ala Asn Asp Ser Gly Glu Thr Met Arg Val Ala
        210                 215                 220

Ile Phe Ala Ser Gly Cys Ser Ser Asp Glu Pro Thr Ser Gln Asn Leu
225                 230                 235                 240

Gly Asn Asn Tyr Ser Asp Glu Pro Cys Ile Gly Gln Glu Tyr Gln Ile
                245                 250                 255

Ile Ala Gln Ile Asn Gly Asn Tyr Ala Arg Leu Leu Asp Thr Val Pro
            260                 265                 270

Leu Asp Tyr Glu Phe Leu Ala Thr Glu Gly Lys Ser Val Cys
        275                 280                 285
```